(12) United States Patent
Woodruff et al.

(10) Patent No.: US 7,410,945 B2
(45) Date of Patent: Aug. 12, 2008

(54) TREATMENT OF INFLAMMATORY BOWEL DISEASE

(75) Inventors: Trent Martin Woodruff, Brisbane (AU); Stephen Maxwell Taylor, Bellbird Park (AU); David Fairlie, Springwood (AU)

(73) Assignee: The University of Queensland, Brisbane (AU)

( * ) Notice: Subject to any disclaimer, the term of this patent is extended or adjusted under 35 U.S.C. 154(b) by 0 days.

(21) Appl. No.: 10/531,564

(22) PCT Filed: Oct. 15, 2003

(86) PCT No.: PCT/AU03/01365

§ 371 (c)(1),
(2), (4) Date: Nov. 1, 2005

(87) PCT Pub. No.: WO2004/035078

PCT Pub. Date: Apr. 29, 2004

(65) Prior Publication Data

US 2006/0135411 A1   Jun. 22, 2006

(30) Foreign Application Priority Data

Oct. 16, 2002  (AU) .............................. 2002952084
May 20, 2003   (AU) .............................. 2003902452

(51) Int. Cl.
*A61K 38/12* (2006.01)
*A61K 38/00* (2006.01)
*A61K 38/04* (2006.01)

(52) U.S. Cl. .............................. 514/9; 514/2; 530/317; 530/329

(58) Field of Classification Search ........................ None
See application file for complete search history.

(56) References Cited

U.S. PATENT DOCUMENTS 5,807,824 A * 9/1998 van Oostrum et al. ......... 514/12

2007/0054841 A1 * 3/2007 Shiels et al. ................... 514/9

FOREIGN PATENT DOCUMENTS

WO   WO 9900406       * 1/1999
WO   WO 9900406 A1 * 1/1999

OTHER PUBLICATIONS

Van Assche G. "Emerging Drugs to Treat Crohn's Disease", 2007, Expert Opin. Emerging Drugs, vol. 12. pp. 49-59.*
Maho Ikeda, et al., Simvastatin Attenuates Trinitrobenzene Sulfonic Acid-Induced Colitis, but Not Oxazalone-Induced Colitis, Springer Science+Business Media, LLC 2007, Oct. 27, 2007, Dig Dis Sci, DOI 10.1007/s10620-007-0102-0.
M. Toulouse, et al., Role of Tachykinin NK2 Receptors in Normal and Altered Rectal Sensitivity in Rats, British Journal of Pharmacology (2000) 129, pp. 193-199, Macmillan Publishers Ltd.
Laurent Diop, et al., Pregabalin (CI-1008) Inhibits the Trinitrobenzene Sulfonic Acid-Induced Chronic Colonic Allodynia in the Rat, The Journal of Pharmacology and Experimental Therapeutics, 2002, pp. 1013-1022, vol. 302, No. 3, http://jpet.aspetjournals.org.
Tetsuya Fukunaga, et al., A Novel Diamino-Pyridine Derivative (IS-741) Attenuates Rat Ileitis Induced by Trinitrobenzene Sulfonic Acid, Journal of Gastroenterology (2003); 38:pp. 451-459, Springer-Verlag 2003.
Gerald P. Morris, et al., Hapten-Induced Model of Chronic Inflammation and Ulceration in the Rat Colon, Gastroenterology (1989) pp. 795-803, vol. 98, American Gastroenterological Association.

* cited by examiner

*Primary Examiner*—Cecilia Tsang
*Assistant Examiner*—Maury Audet
(74) *Attorney, Agent, or Firm*—Haynes and Boone, LLP; Mark D. Moore

(57) ABSTRACT

This invention relates to methods of treatment of inflammatory bowel disease, and especially to treatment of this condition with cyclic peptidic and peptidomimetic compounds which have the ability to modulate the activity of G protein-coupled receptors. The compounds preferably act as antagonists of the C5a receptor, and are active against C5a receptors on polymorphonuclear leukocytes and macrophages. Particularly preferred compounds for use in the methods of the invention are disclosed.

9 Claims, 8 Drawing Sheets

TREATMENT OF INFLAMMATORY BOWEL DISEASE

FIELD OF THE INVENTION

This invention relates to the treatment of inflammatory bowel disease, and especially to treatment of this condition with novel cyclic peptidic and peptidomimetic compounds which have the ability to modulate the activity of G protein-coupled receptors. The compounds preferably act as antagonists of the C5a receptor, and are active against C5a receptors on polymorphonuclear leukocytes and macrophages.

BACKGROUND OF THE INVENTION

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in Australia or in any other country.

G protein-coupled receptors are prevalent throughout the human body, comprising approximately 60% of known cellular receptor types, and mediate signal transduction across the cell membrane for a very wide range of endogenous ligands. They participate in a diverse array of physiological and pathophysiological processes, including, but not limited to those associated with cardiovascular, central and peripheral nervous system, reproductive, metabolic, digestive, immunological, inflammatory, and growth disorders, as well as other cell-regulatory and proliferative disorders. Agents which selectively modulate functions of G protein-coupled receptors have important therapeutic applications. These receptors are becoming increasingly recognised as important drug targets, due to their crucial roles in signal transduction (G protein-coupled Receptors, IBC Biomedical Library Series, 1996).

One of the most intensively studied G protein-coupled receptors is the receptor for C5a. C5a is one of the most potent chemotactic agents known, and recruits neutrophils and macrophages to sites of injury, alters their morphology; induces degranulation; increases calcium mobilisation, vascular permeability (oedema) and neutrophil adhesiveness; contracts smooth muscle; stimulates release of inflammatory mediators, including histamine, TNF-α, IL-1, IL-6, IL-8, prostaglandins, and leukotrienes, and of lysosomal enzymes; promotes formation of oxygen radicals; and enhances antibody production (Gerard and Gerard, 1994).

Agents which limit the pro-inflammatory actions of C5a have potential for inhibiting chronic inflammation, and its accompanying pain and tissue damage. For these reasons, molecules which prevent C5a from binding to its receptors are useful for treating chronic inflammatory disorders driven by complement activation. Because such compounds act upstream from the various inflammatory mediators referred to above, and inhibit the formation of many of these compounds, they may have a more powerful effect in alleviating or preventing inflammatory symptoms.

In our previous application No. PCT/AU98/00490, we described the three-dimensional structure of some analogues of the C-terminus of human C5a, and used this information to design novel compounds which bind to the human C5a receptor (C5aR), behaving as either agonists or antagonists of C5a. It had previously been thought that a putative antagonist might require both a C-terminal arginine and a C-terminal carboxylate for receptor binding and antagonist activity (Konteatis et al, 1994). We showed that in fact a terminal carboxylate group is not generally required either for high affinity binding to C5aR or for antagonist activity. Instead we found that a hitherto unrecognised structural feature, a turn conformation, was the key recognition feature for high affinity binding to the human C5a receptor on neutrophils. As described in our international patent application No. PCT/AU02/01427, filed on 17th Oct. 2002, we used further refinements of these findings to design more tightly constrained structural templates which enable hydrophobic groups to be assembled into a hydrophobic array for interaction with a C5a receptor. We have subsequently found that a preferred compound of this class is able to inhibit cardiac and pulmonary fibrosis, and this is described in our international patent application No. PCT/AU03/00415, filed on 7th Apr. 2003. The entire disclosures of these specifications are incorporated herein by this reference.

Inflammatory bowel disease (IBD) is a group of serious, chronic relapsing inflammatory diseases affecting both the small and large intestine, which remains relatively resistant to current treatments. IBD is characterized by spontaneously occurring, chronic relapsing inflammation of unknown origin, in which current treatment options are inadequate (reviewed by van Deventer, 2002). Despite extensive research into the disease in both humans and experimental animals, the precise mechanisms of pathology remain to be elucidated. A host of immune and inflammatory mediators are thought to be involved, including biogenic amines, kinins, arachidonic acid metabolites, free radicals, nitric oxide, various proinflammatory cytokines, and complement proteins (Nielsen et al, 1996). Recent advances in drug development for IBD have involved the use of monoclonal antibodies to inhibit pro-inflammatory cytokines, such as interleukins, interferons and tumour necrosis factor α (TNF-α). In particular, the anti-TNF-α antibodies CDP571 and infliximab have been used clinically to treat Crohn's disease with some success. However, these new protein therapies suffer from major drawbacks, such as the costs of production, instability, poor bioavailability, limited routes of administration, and immunogenicity.

Several major forms of IBD are known, and Crohn's disease (regional bowel disease) and ulcerative colitis are the most common of these disorders. Because of the nature of their pathology, there are a number of autoimmune and immune-mediated diseases of the small and large bowel which are likely to benefit from treatment with these C5a antagonists. These include lymphocytic-plasmocytic enteritis, coeliac disease, collagenous colitis, lymphocytic colitis and eosinophilic enterocolitis. Other less common forms of IBD include indeterminate colitis, infectious colitis (viral, bacterial or protozoan, e.g. amoebic colitis), pseudomembranous colitis (necrotizing colitis), and ischemic inflammatory bowel disease. These conditions have been diagnosed in humans and in a number of animal species.

In 1999, approximately 1.7 million people in the United States alone were diagnosed with this debilitating disease. Satisfactory treatment of IBD is an unmet medical need, as existing therapeutic agents have not been successful in curtailing the disease and avoiding the need for surgery. Up to 40% of all ulcerative colitis patients undergo surgery, which typically includes either the removal of part of the large intestine or a full colostomy. While surgery is not curative for Crohn's disease, 75% of all patients will undergo at least one surgery in their lifetime, and up to 90% of these patients require additional surgeries. A therapeutic agent which can successfully treat inflammatory bowel disease can enormously improve a patient's quality of life, while potentially saving the healthcare system millions of dollars in costs associated with invasive surgical procedures.

In these conditions, chronic inflammation, caused by a number of inflammatory mediators, has been implicated in pathogenesis. The complement system has been acknowledged as one of these inflammatory mediators, since increased levels of complement products are found in the colons of patients with IBD (Neilsen et al. 1996). Ulcerative colitis, also known as idiopathic colitis, is characterized by inflammation of the colon and rectum, which become inflamed and ulcerated; its cause is unclear, although antibodies to colonic epithelium and *E. coli* strain 0119 B14 are often present. Its severity varies, and the patients suffer frequent relapses. Crohn's disease, also called regional enteritis or regional ileitis, is characterized by inflammation, thickening and ulceration of the bowel wall, usually in the terminal part of the ileum, with oedematous mucosa or thickened soft tissue, mesenteric infiltration, thickened bowel wall, and often inflammatory masses, abscesses, or distended fluid-filled loops. Complications include fistulae, intramural sinus tracts, abscesses, perforations, toxic megacolon, obstruction of the bowel, or hydronephrosis, and there is an increased risk of adenocarcinoma in the ileum or colon.

In both these conditions extensive bed rest is often required, and in severe case the affected part of the bowel may be surgically removed, necessitating the use of an ostomy bag. The only therapeutic agents which are available are corticosteroids such as prednisolone, monoclonal antibodies directed against tumour necrosis factor, such as Remicade (infliximab), immunosuppressive agents such as methotrexate, azathioprine, cyclosporine, tacrolimus and mycophenolate mofetil, or other anti-inflammatory agents such as sulphasalazine. These agents, especially the steroids, may be of limited effectiveness, and may have serious side effects. A variety of other agents, including corticosteroid derivatives such as budesonide, antagonists and agonists of cytokines such as interleukin-10 and interleukin-11, and a nicotinic receptor agonist, are in various stages of clinical trial. To our knowledge none of these approved or experimental agents, and in particular no small molecule agent, targets the C5a receptor.

Therefore there is a great need in the art for effective, non-toxic agents which do not require administration by injection, and which can be produced at reasonable cost.

SUMMARY OF THE INVENTION

Because of the lack of knowledge of complement involvement in IBD, we tested the possible inhibitory effects of specific complement inhibitors in an animal model of colitis. We now show for the first time that a specific inhibitor of the C5a receptor is able to ameliorate signs of damage in trinitrobenzenesulphonic acid (TNBS)-induced colitis in rats. This model has been used extensively to investigate the pathogenesis of IBD (Morris et al, 1989). We found strong protective effects for antagonists of both C3a and C5a, suggesting a large and previously undefined role for complement as a mediator of IBD.

This is the first reported case of an inhibitor of the complement system being used to modulate pathology in a model of IBD.

Complement is therefore a potential target for therapeutic intervention in inflammatory bowel disease.

According to a first aspect, the invention provides a method of treatment of inflammatory bowel disease (IBD), comprising the step of administering an effective amount of an inhibitor of a G protein-coupled receptor to a subject in need of such treatment.

Preferably the a inhibitor is a compound which
a) is an antagonist of a G protein-coupled receptor,
b) has substantially no agonist activity, and
c) is a cyclic peptide or peptidomimetic compound of formula I

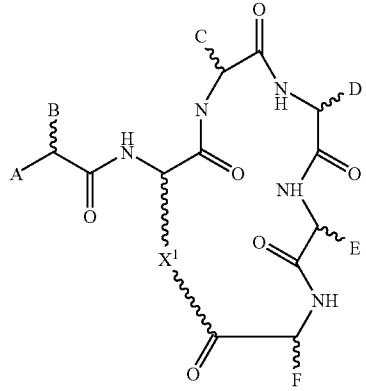

where A is H, alkyl, aryl, $NH_2$, NH-alkyl, $N(alkyl)_2$, NH-aryl, NH-acyl, NH-benzoyl, $NHSO_3$, $NHSO_2$-alkyl, $NHSO_2$-aryl, OH, O-alkyl, or O-aryl;

B is an alkyl, aryl, phenyl, benzyl, naphthyl or indole group, or the side chain of a D- or L-amino acid such as L-phenylalanine or L-phenylglycine, but is not the side chain of glycine, D-phenylalanine, L-homophenylalanine, L-tryptophan, L-homotryptophan, L-tyrosine, or L-homotyrosine;

C is a small substituent, such as the side chain of a D-, L- or homo-amino acid such as glycine, alanine, leucine, valine, proline, hydroxyproline, or thioproline, but is preferably not a bulky substituent such as isoleucine, phenylalanine, or cyclohexylalanine;

D is the side chain of a neutral D-amino acid such as D-Leucine, D-homoleucine, D-cyclohexylalanine, D-homocyclohexylalanine, D-valine, D-norleucine, D-homo-norleucine, D-phenylalanine, D-tetrahydroisoquinoline, D-glutamine, D-glutamate, or D-tyrosine, but is preferably not a small substituent such as the side chain of glycine or D-alanine, a bulky planar side chain such as D-tryptophan, or a bulky charged side chain such as D-arginine or D-Lysine;

E is a bulky substituent, such as the side chain of an amino acid selected from the group consisting of L-phenylalanine, L-tryptophan and L-homotryptophan, or is L-1-napthyl or L-3-benzothienyl alanine, but is not the side chain of D-tryptophan, L-N-methyltryptophan, L-homophenylalanine, L-2-naphthyl L-tetrahydroisoquinoline, L-cyclohexylalanine, D-leucine, L-fluorenylalanine, or L-histidine;

F is the side chain of L-arginine, L-homoarginine, L-citrulline, or L-canavanine, or a bioisostere thereof, ie. a side chain in which the terminal guanidine or urea group is retained, but the carbon backbone is replaced by a group which has different structure but is such that the side chain as a whole reacts with the target protein in the same way as the parent group; and X is —$(CH_2)_n$NH— or —$(CH_2)_n$—S—, where n is an integer of from 1 to 4, preferably 2 or 3; —$(CH_2)_2$O—; —$(CH_2)_3$O—; —$(CH_2)_3$—; —$(CH_2)_4$—; —$CH_2$COCHRNH—; or —$CH_2$—chain of any common or uncommon amino acid.

In C, both the cis and trans forms of hydroxyproline and thioproline may be used.

Preferably A is an acetamide group, an aminomethyl group, or a substituted or unsubstituted sulphonamide group.

Preferably where A is a substituted sulphonamide, the substituent is an alkyl chain of 1 to 6, preferably 1 to 4 carbon atoms, or a phenyl or toluyl group.

In a particularly preferred embodiment, the compound has antagonist activity against C5aR, and has no C5a agonist activity.

The compound is preferably an antagonist of C5a receptors on human and mammalian cells including, but not limited to, human polymorphonuclear leukocytes and human macrophages. The compound preferably binds potently and selectively to C5a receptors, and more preferably has potent antagonist activity at sub-micromolar concentrations. Even more preferably the compound has a receptor affinity IC50<25 µM, and an antagonist potency IC50□|µ□

Most preferably, the compound is selected from the group consisting of AcF-[OPdChaWR]—also referred to herein as "PMX53" and "(AcPhe[Orn-Pro-D-Cyclohexylalanine-Trp-Arg])".

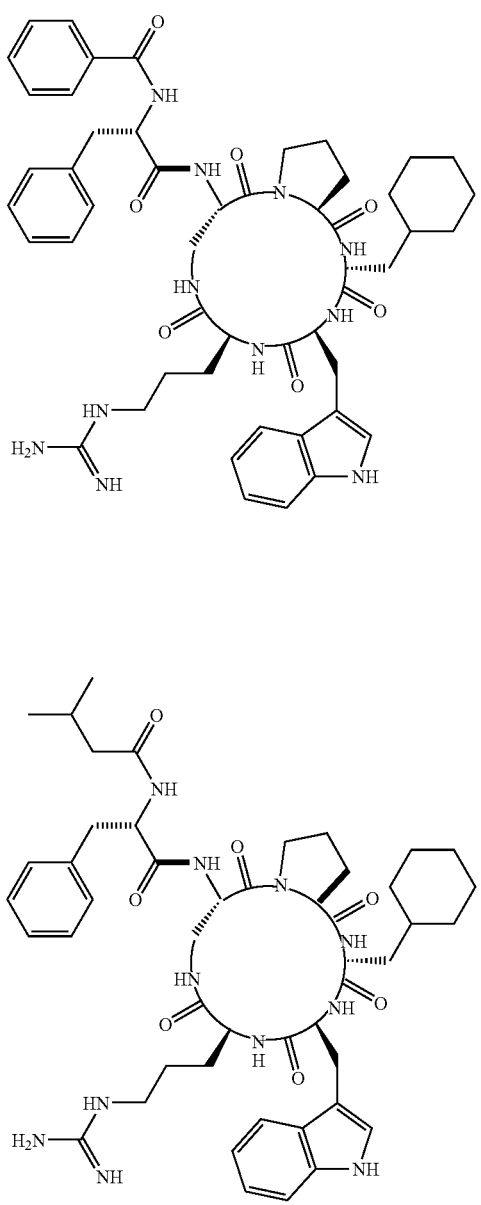

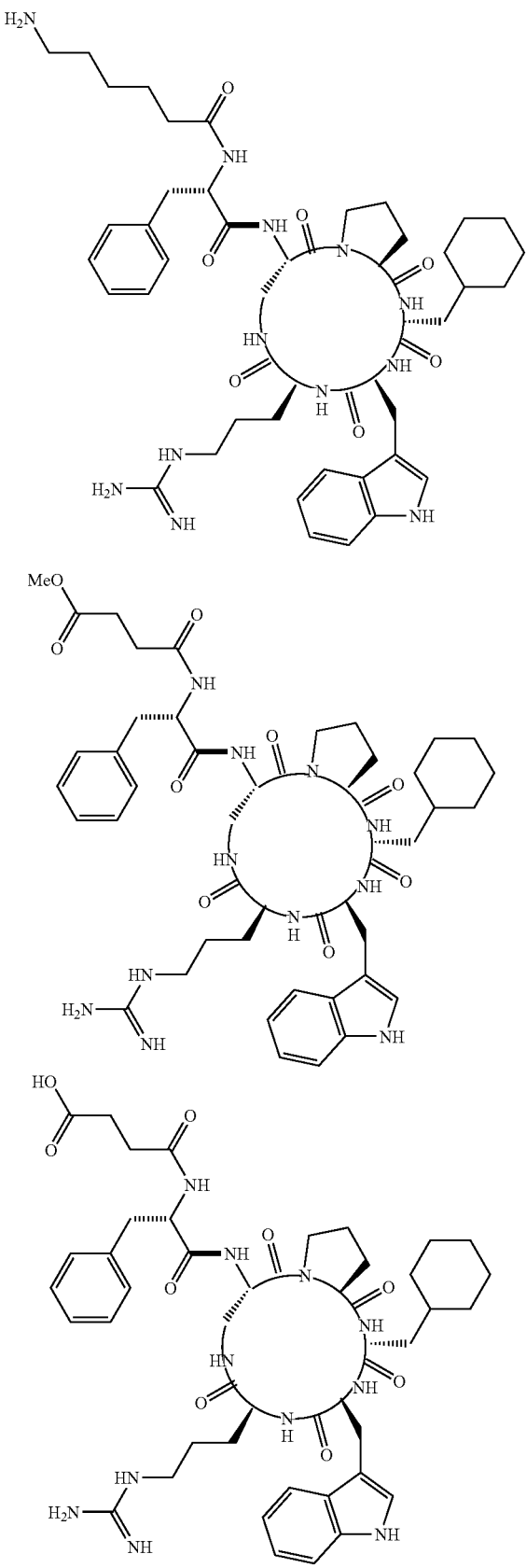

10
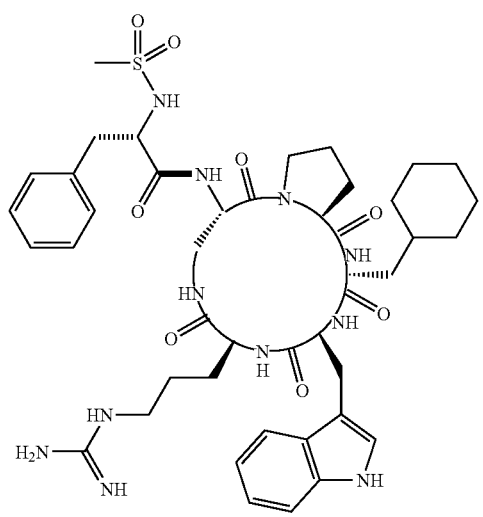
11
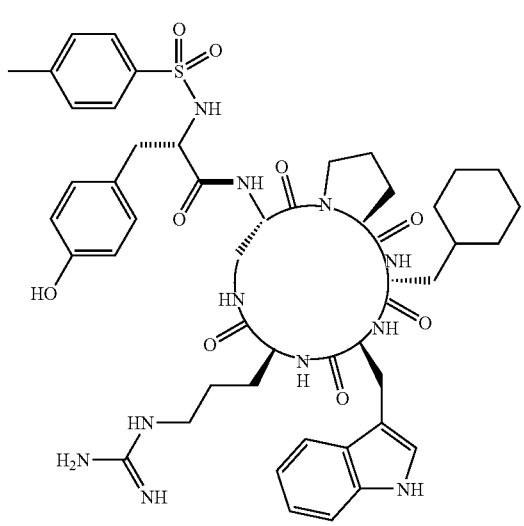
12
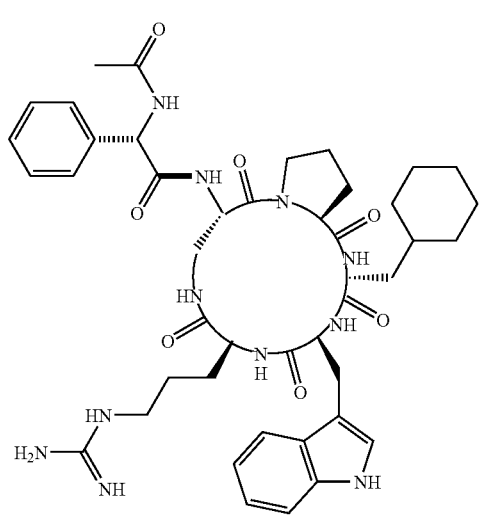
13
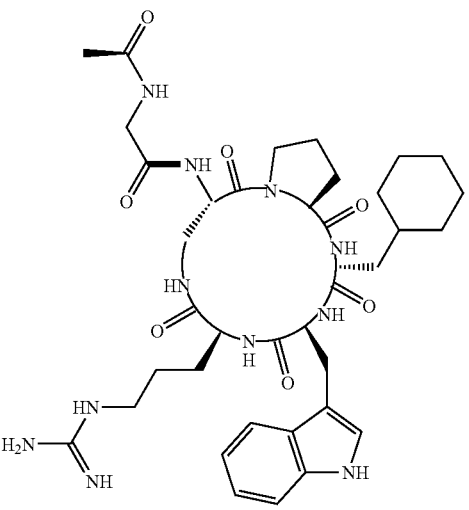
14
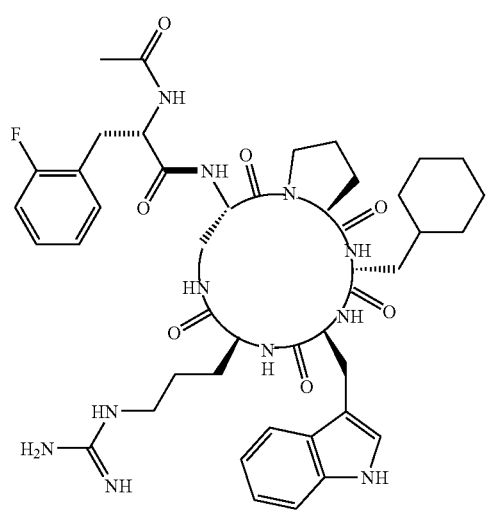
15
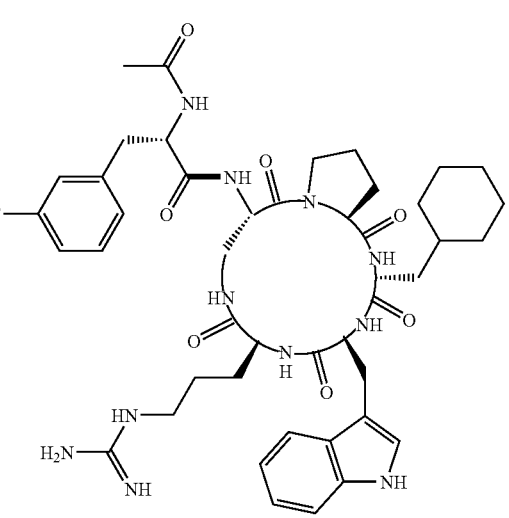

17
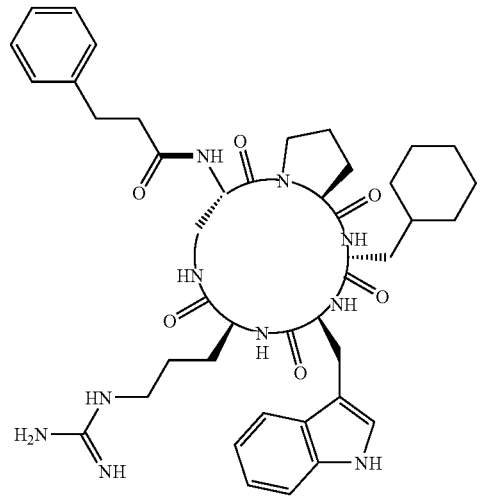
19
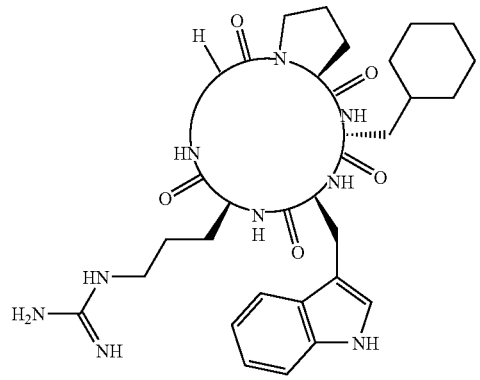
20
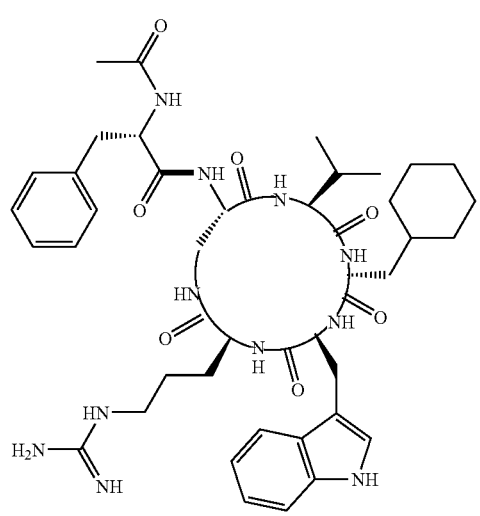
22
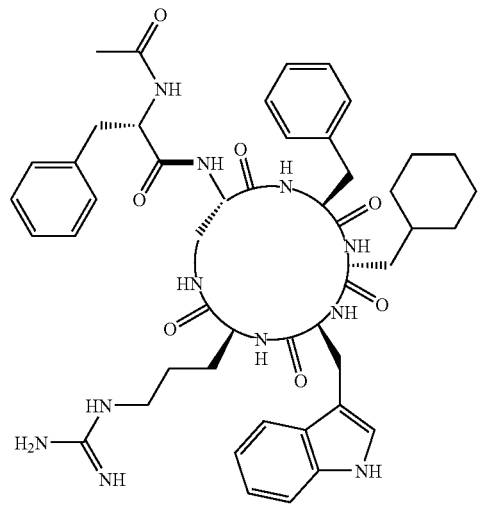
25
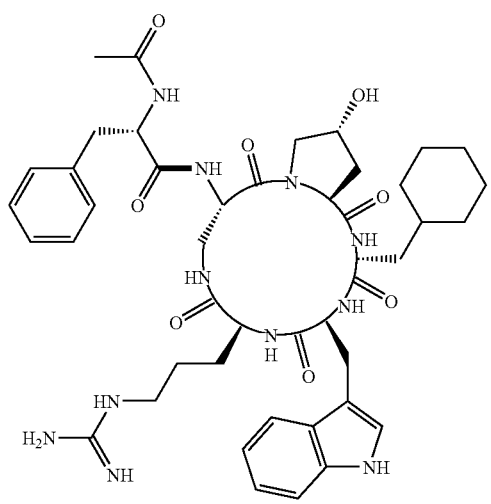
26
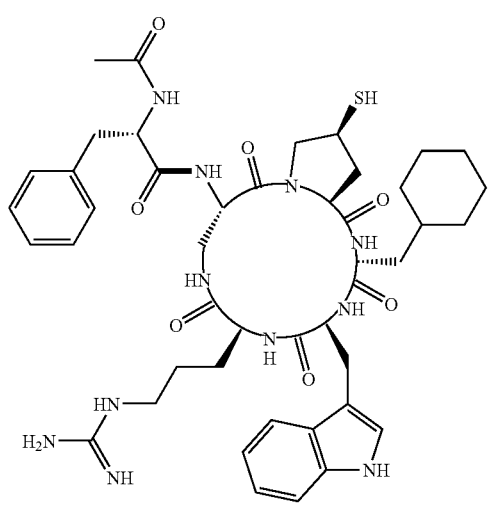

-continued
27
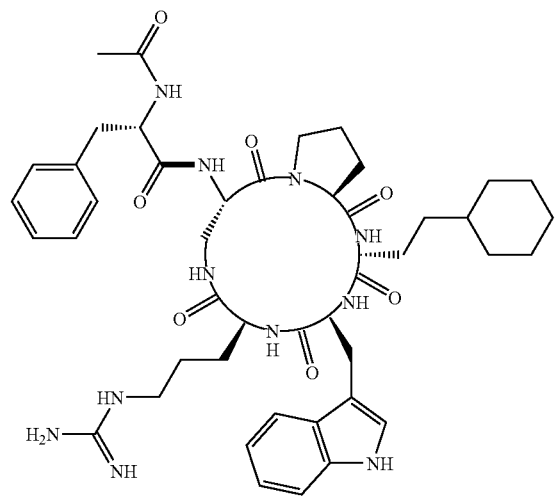
30
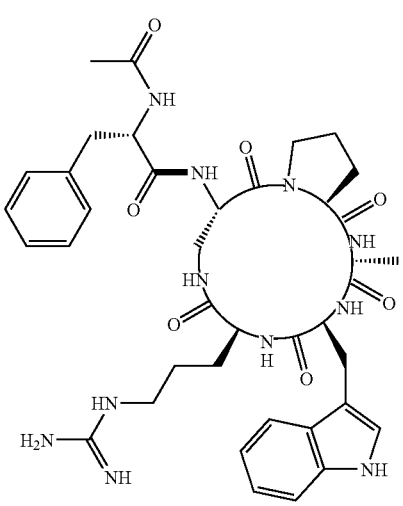
31
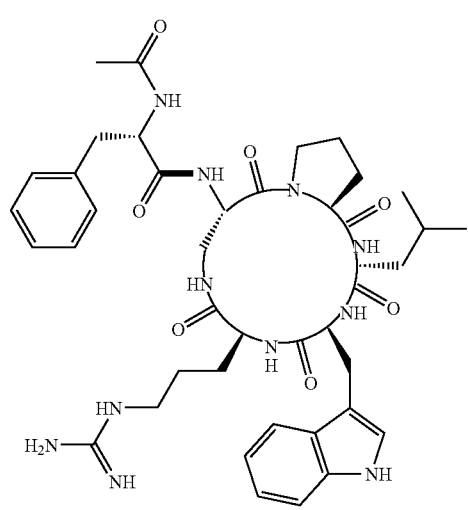
-continued
33
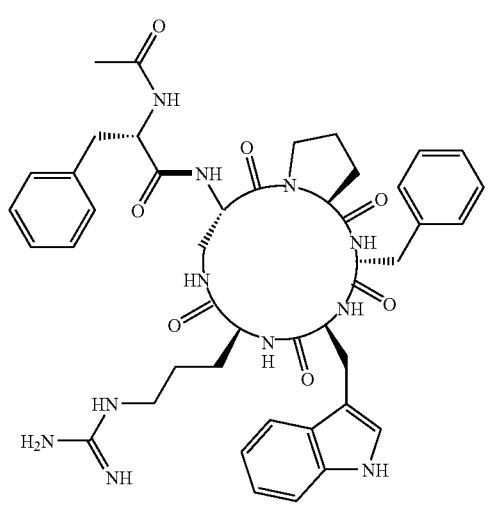
34
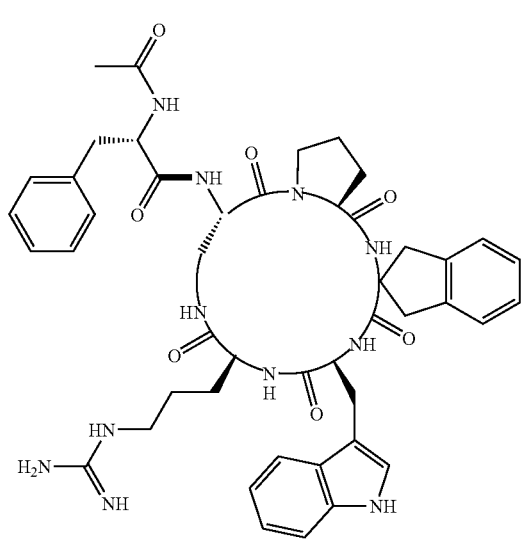
35
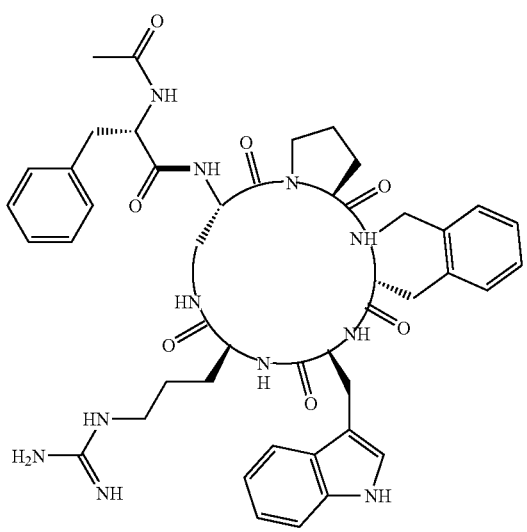

36
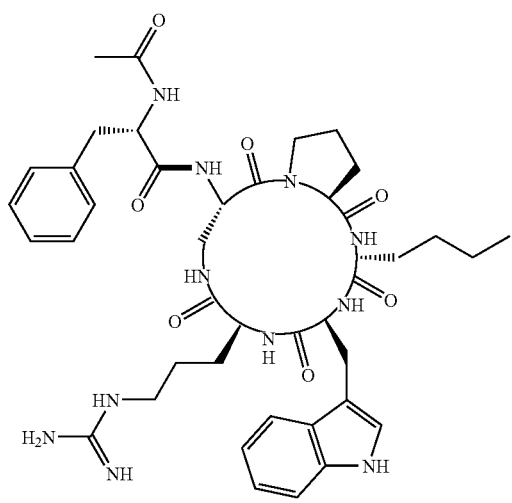
37
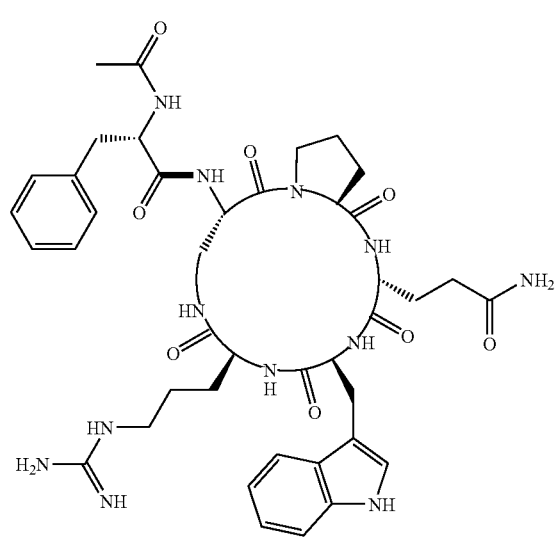
39
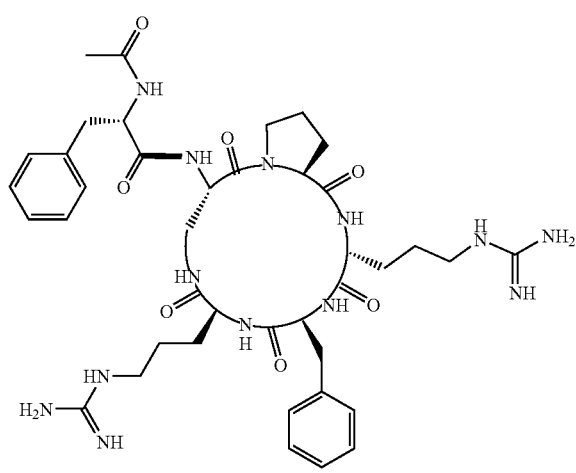
40
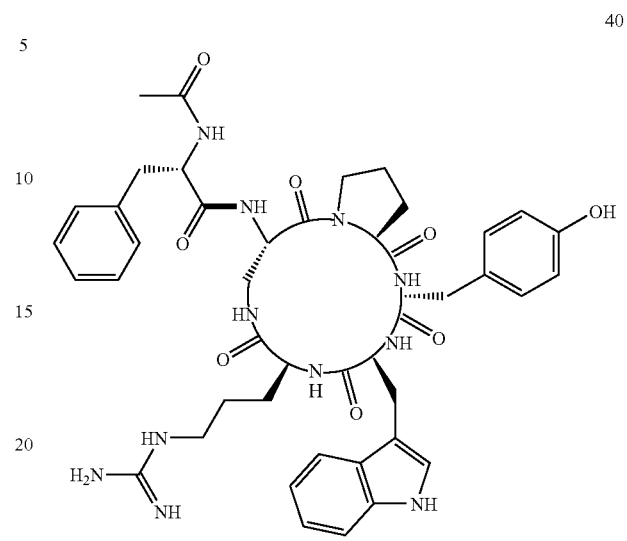
41
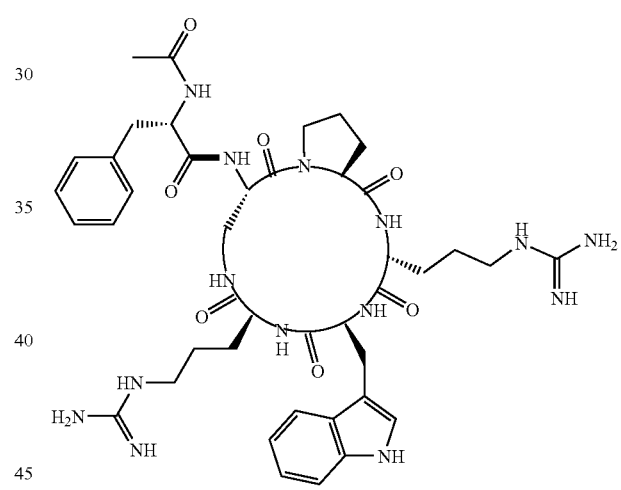
42
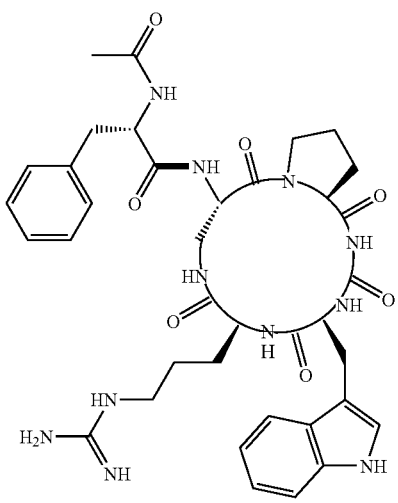

43
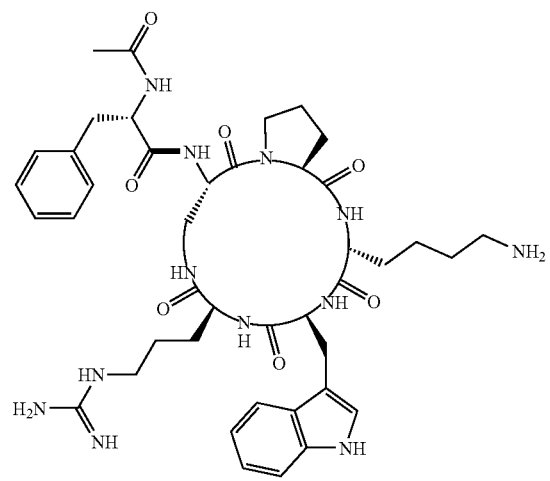
44
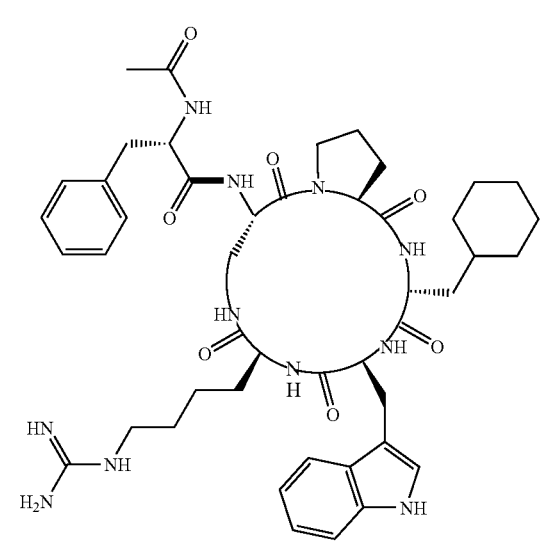
45
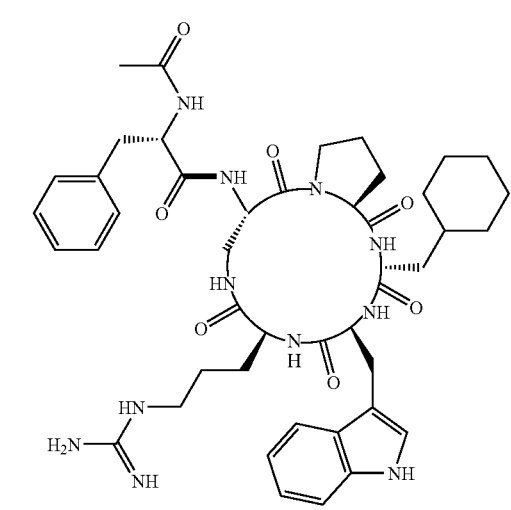
46
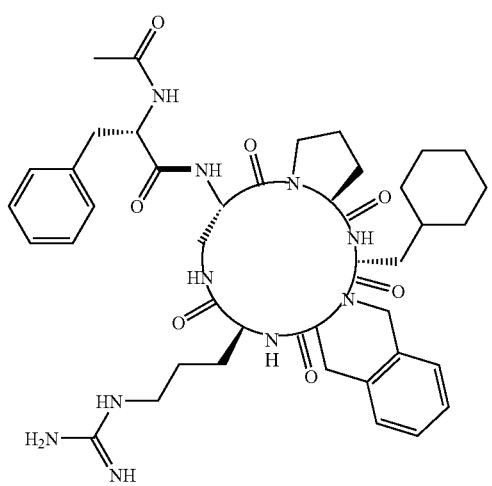
57
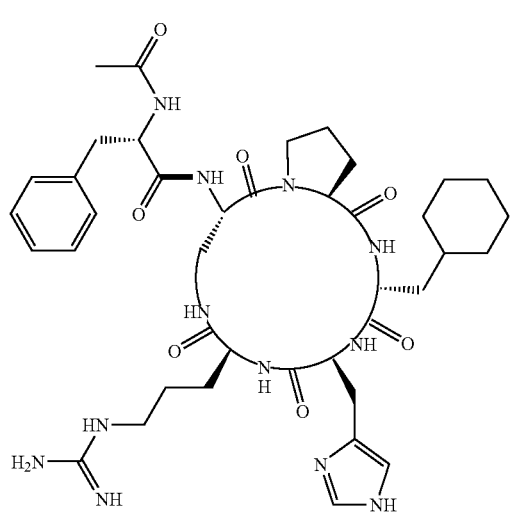
58
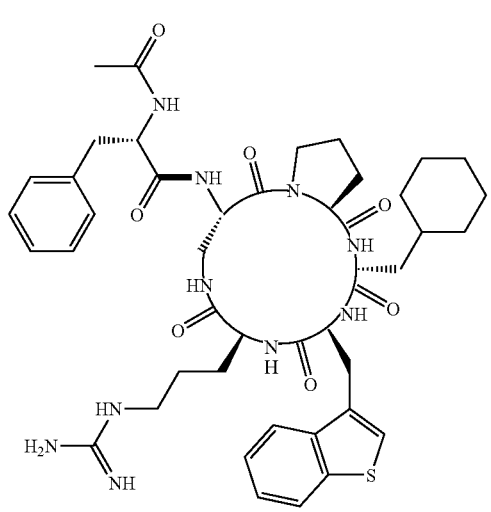

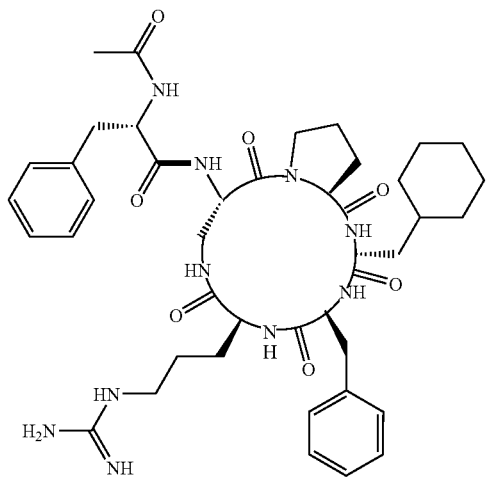

60

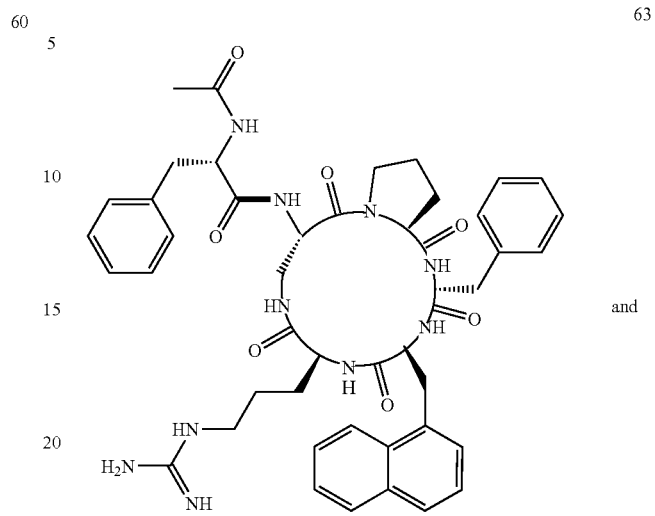

63 and

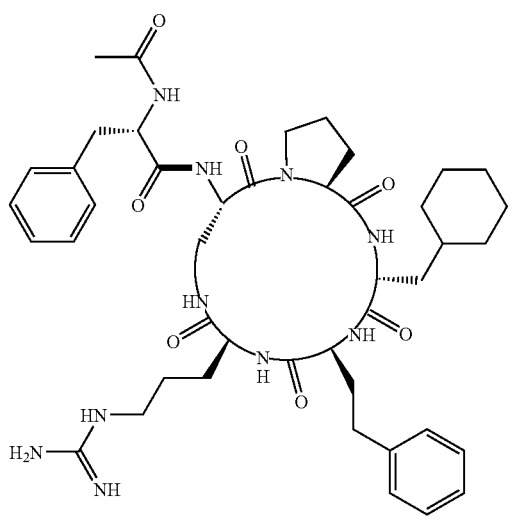

61

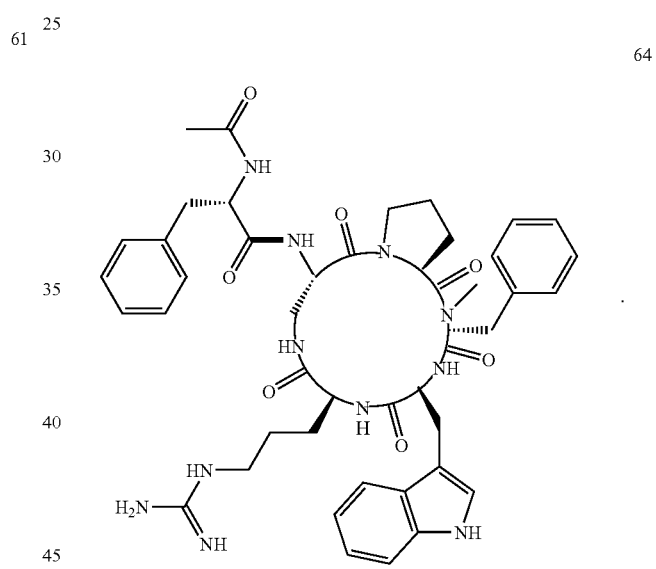

64

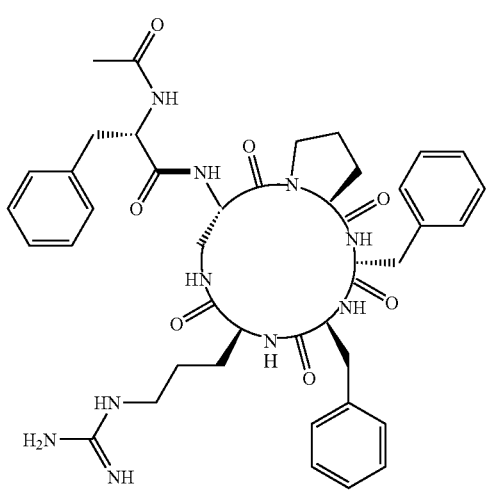

62

In a second aspect the invention provides the use of a compound as defined above in the manufacture of a medicament for the treatment of inflammatory bowel disease.

The inhibitor may be used in conjunction with one or more other agents for the treatment of IBD, including but not limited to corticosteroids such as prednisolone and budesonide, other immunosuppressive agents such as infliximab (Remicade; Johnson & Johnson), methotrexate or azathioprine, anti-inflammatory agents such as sulphasalazine, Colazal (balsalazide), and the like, and probiotics.

We have demonstrated herein that a C3a inhibitor, SB 290157, is also able to modulate the pathology of IBD in an animal model system, and so it is contemplated that a combination of a C5a inhibitor and a C3a inhibitor will be useful in the treatment of this condition.

The compositions of the invention may be formulated for oral, parenteral, inhalational, intranasal, per rectum (intracolonic) or transdermal use, but oral or per rectum formulations are preferred. Suitable formulations for administration by any desired route may be prepared by standard methods, for example by reference to well-known textbooks such as Remington: The Science and Practice of Pharmacy, Vol. II, 2000 ($20^{th}$ edition), A. R. Gennaro (ed), Williams & Wilkins, Pennsylvania.

Preferred formulations include enteric coated capsules, or per-rectal (intra-colonic) dosage forms such as enemas, to facilitate absorption in the colon, the local area of inflammation.

The method of the invention is applicable to the treatment of any form of inflammatory bowel disease, including but not limited to Crohn's disease (regional bowel disease); ulcerative colitis; autoimmune and immune-mediated diseases of the small and large bowel such as lymphocytic-plasmocytic enteritis, coeliac disease, collagenous colitis, lymphocytic colitis and eosinophilic enterocolitis; indeterminate colitis, infectious colitis (viral, bacterial or protozoan, e.g. amoebic colitis), pseudomembranous colitis (necrotizing colitis), and ischemic inflammatory bowel disease.

While the invention is not in any way restricted to the treatment of any particular animal or species, it is particularly contemplated that the method of the invention will be useful in medical treatment of humans, and will also be useful in veterinary treatment, particularly of companion animals such as cats and dogs, livestock such as cattle, horses and sheep, and zoo animals, including non-human primates, large bovids, felids, ungulates and canids. For example, felines and particularly canines suffer from a variety of inflammatory enteropathies which have some similarities to IBD in humans. These include enterocolitis, canine plasmacytic-lymphocytic colitis, protothecal colitis, and histiocytic ulcerative colitis.

The compound may be administered at any suitable dose and by any suitable route. Oral or rectal administration is preferred, because of the greater convenience and acceptability of these routes. It is expected that most if not all compounds of the invention will be stable in the presence of metabolic enzymes, such as those of the gut, blood, lung or intracellular enzymes. Such stability can readily be tested by routine methods known to those skilled in the art.

The effective dose will depend on the nature of the condition to be treated, and the age, weight, and underlying state of health of the individual treatment. This will be at the discretion of the attending physician or veterinarian. Suitable dosage levels may readily be determined by trial and error experimentation, using methods which are well known in the art.

DETAILED DESCRIPTION OF THE INVENTION

Figure 1:
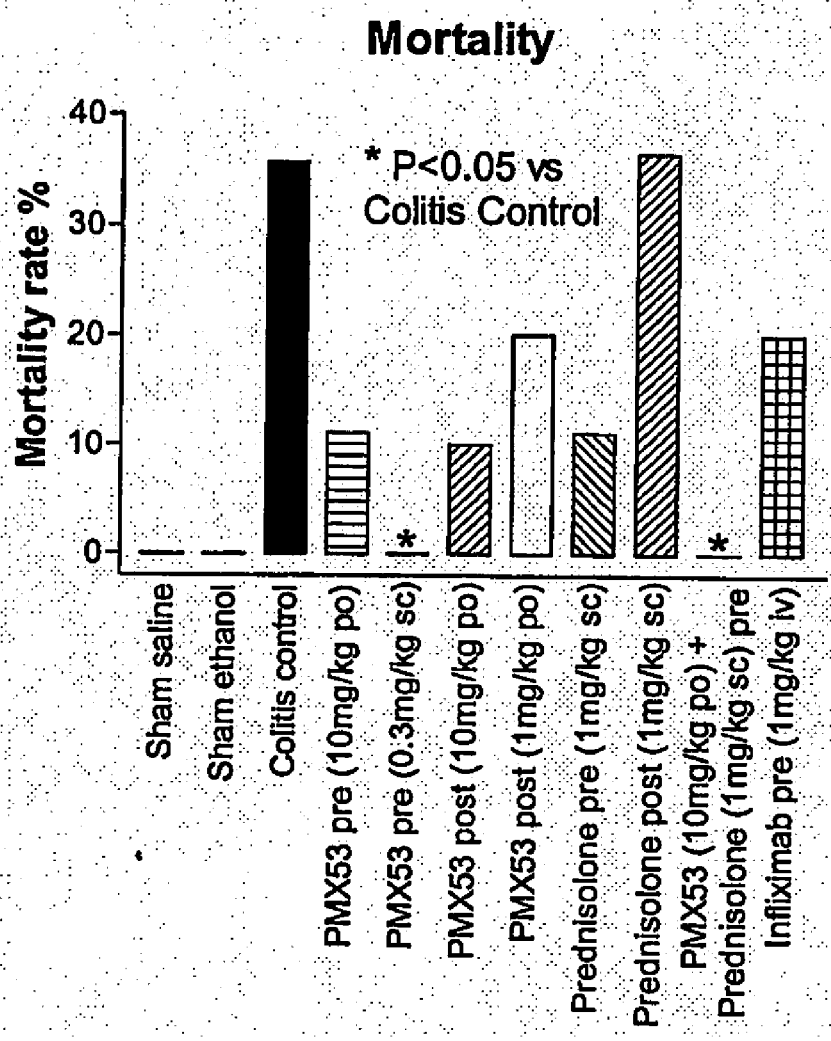
FIG. 1 shows the effect on mortality rate over 8 days. pre=pre-treatment; post=post-treatment.
Figure 2:
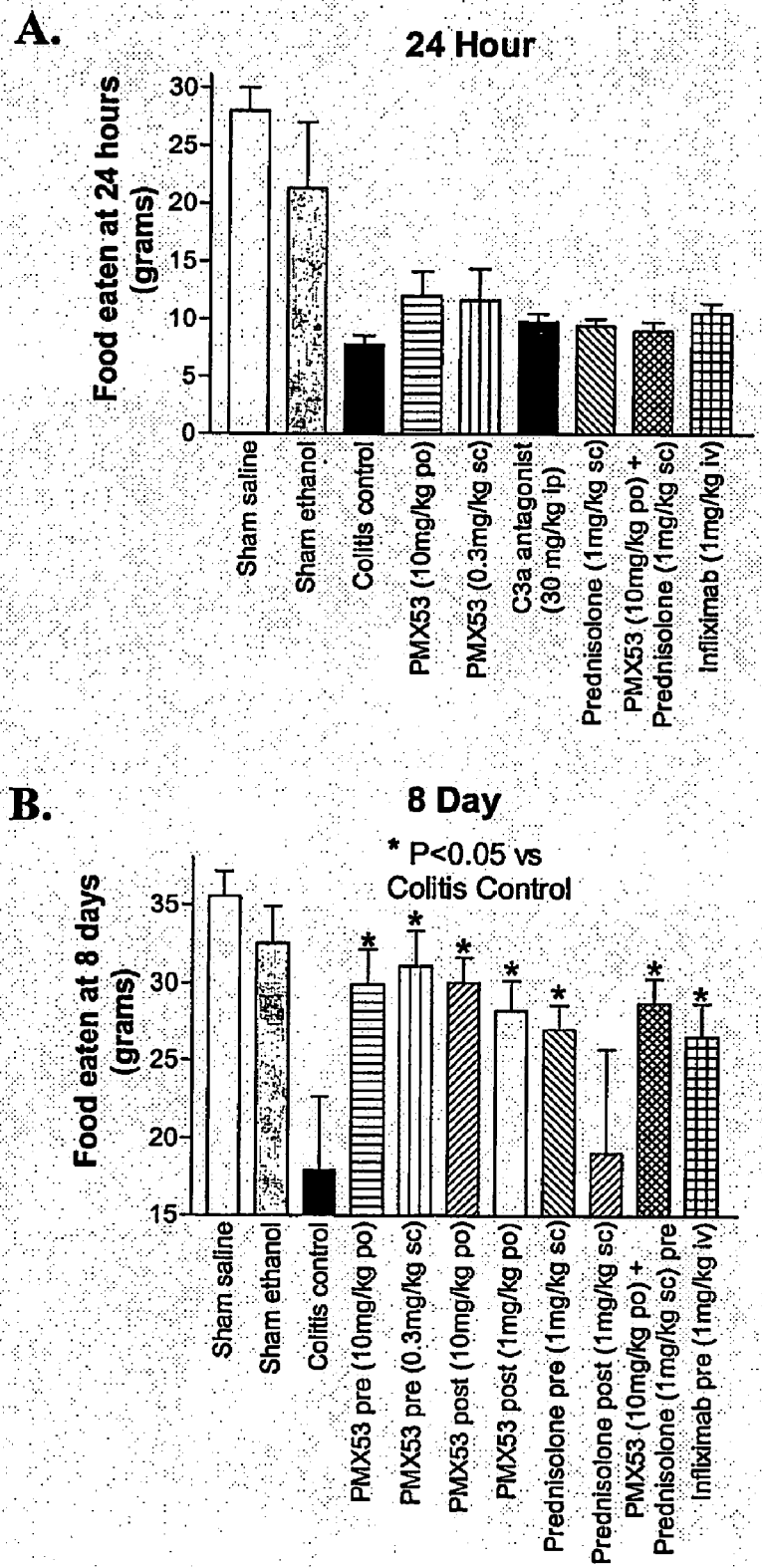
FIG. 2 shows the effect on food consumption. The amount of food consumed was measured either after 24 h [A] or at 8 days [B]. Data represent the mean±SEM (n=4-12). *$P<0.05$ drug-treated rats vs. colitis control. pre=pre-treatment; post=post-treatment.
Figure 3:
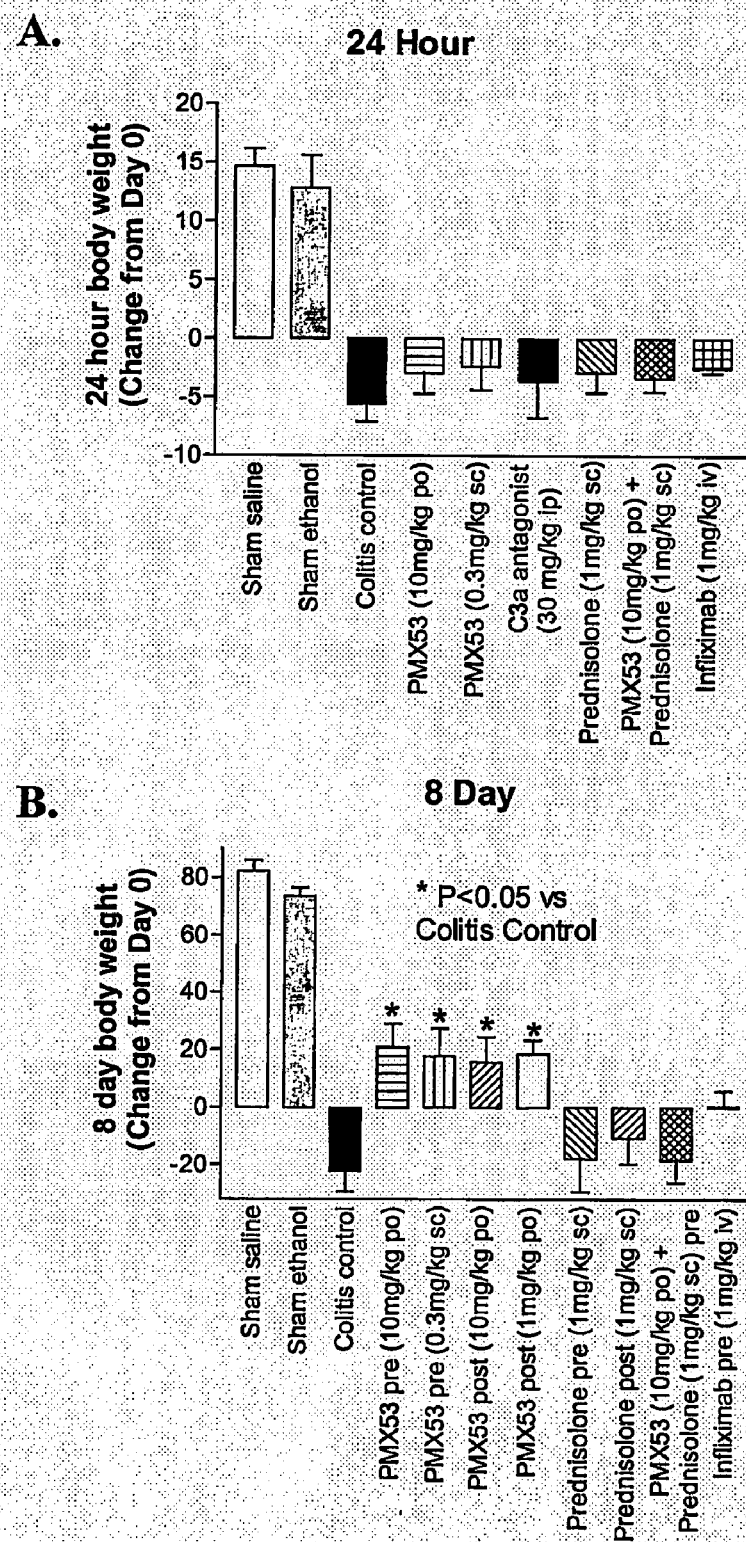
FIG. 3 shows the effect on body weight. The change in body weight following TNBS administration was measured after either [A] 24 h or [B] 8 days. Data represent the mean±SEM (n=4-12). *$P<0.05$ drug-treated rats vs. colitis control. pre=pre-treatment; post=post-treatment.
Figure 4:
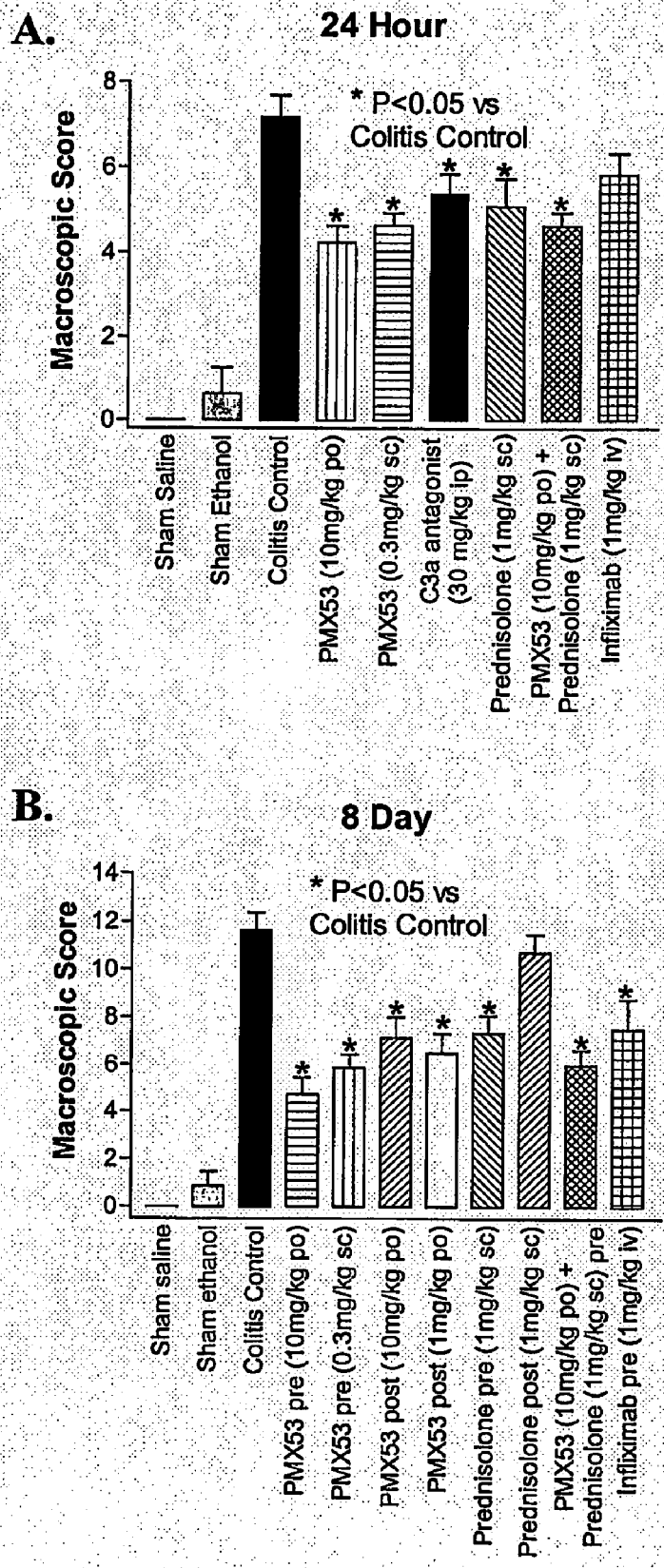
FIG. 4 summarizes the clinical macroscopic scores. The colons were scored for macroscopic damage on a scale of 0-13 at either [A] 24 h or [B] 8 days. Data represent the mean±SEM (n=4-12). *$P<0.05$ drug-treated rats vs. colitis control pre=pre-treatment; post 15=post-treatment.
Figure 5:
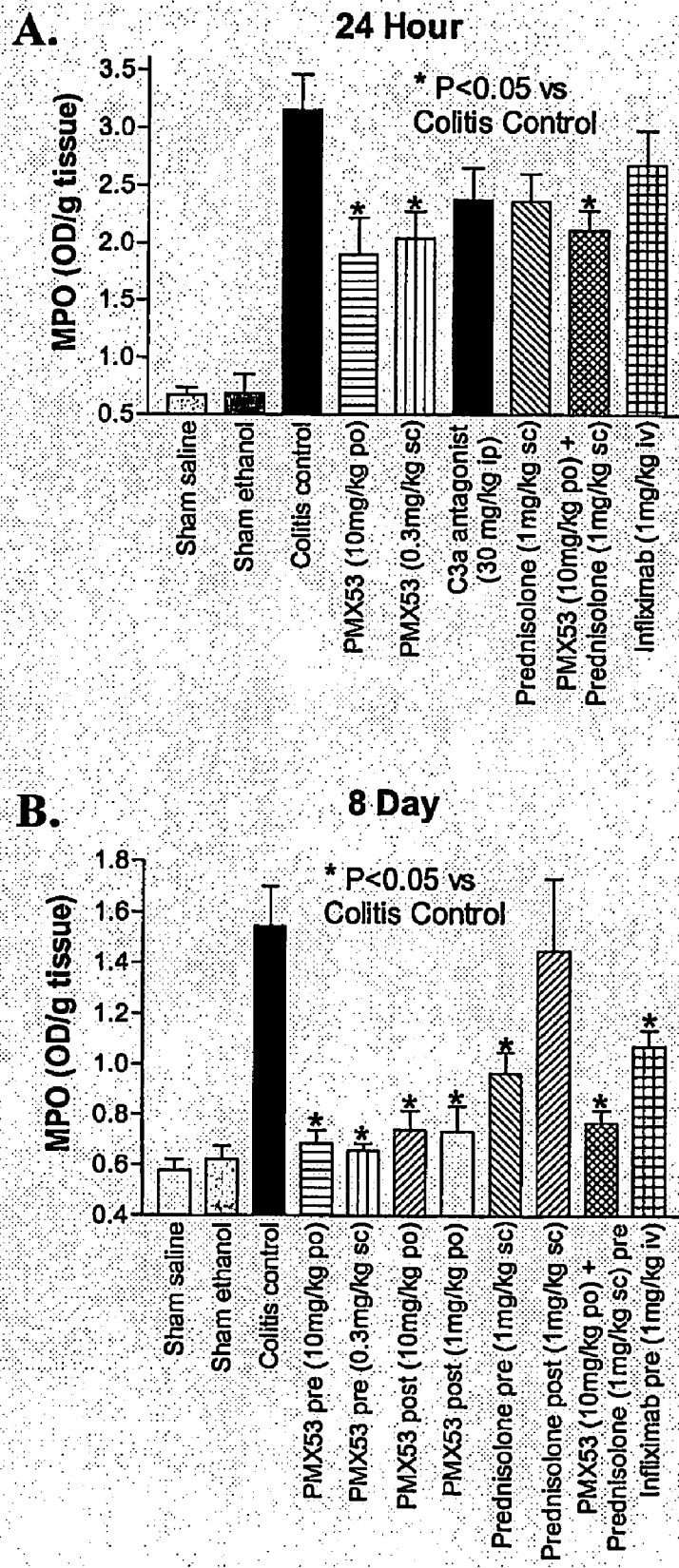
FIG. 5 shows the effect on colon myeloperoxidase (MPO) levels. Levels of MPO in rat's colons were measured at either [A] 24 h or [B] 8 days. Data represent the mean±SEM (n=4-12). *$P<0.05$ drug-treated rats vs. colitis control. pre=pre-treatment; post=post-treatment.

It is to be clearly understood that this invention is not limited to the particular materials and methods described herein, as these may vary. It is also to be understood that the terminology used herein is for the purpose of describing particular embodiments only, and it is not intended to limit the scope of the present invention, which will be limited only by the appended claims.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

As used herein, the singular forms "a", "an", and "the" include plural reference unless the context clearly dictates otherwise. Thus, for example, a reference to "an enzyme" includes a plurality of such enzymes, and a reference to "an amino acid" is a reference to one or more amino acids. Unless defined otherwise, all technical and scientific terms used herein have the same meaning as commonly understood by one of ordinary skill in the art to which this invention belongs. Although any materials and methods similar or equivalent to those described herein can be used to practice or test the present invention, the preferred materials and methods are now described.

Abbreviations used herein are as follows:
Cit citrulline
dCha D-cyclohexylamine
DPhe D-phenylalanine
IBD inflammatory bowel disease
ip intraperitoneal
iv intravenous
LPS lipopolysaccharide
MPO myeloperoxidase PMN polymorphonuclear granulocyte
PMSF phenylmethylsulfonyl fluoride
Pr per rectum
sc subcutaneous
TNBS trinitrobenzenesulphonic acid
TNF-α tumour necrosis factor-α

Throughout the specification conventional single-letter and three-letter codes are used to represent amino acids.

For the purposes of this specification, the term "alkyl" is to be taken to mean a straight, branched, or cyclic, substituted or unsubstituted alkyl chain of 1 to 6, preferably 1 to 4 carbons. Most preferably the alkyl group is a methyl group. The term "acyl" is to be taken to mean a substituted or unsubstituted acyl of 1 to 6, preferably 1 to 4 carbon atoms. Most preferably the acyl group is acetyl. The term "aryl" is to be understood to mean a substituted or unsubstituted homocyclic or heterocyclic aryl group, in which the ring preferably has 5 or 6 members.

A "common" amino acid is a L-amino acid selected from the group consisting of glycine, leucine, isoleucine, valine, alanine, phenylalanine, tyrosine, tryptophan, aspartate, asparagine, glutamate, glutamine, cysteine, methionine, arginine, lysine, proline, serine, threonine and histidine.

An "uncommon" amino acid includes, but is not restricted to, D-amino acids, homo-amino acids, N-alkyl amino acids, dehydroamino acids, aromatic amino acids other than phenylalanine, tyrosine and tryptophan, ortho-, meta- or para-aminobenzoic acid, ornithine, citruhlline, canavanine, norleucine, -glutamic acid, aminobutyric acid, L-fluorenylalanine, L-3-benzothienylalanine, and α, α-disubstituted amino acids.

Generally, the terms "treating", "treatment" and the like are used herein to mean affecting a subject, tissue or cell to obtain a desired pharmacological and/or physiological effect. The effect may be prophylactic in terms of completely or partially preventing a disease or sign or symptom thereof, and/or may be therapeutic in terms of a partial or complete cure of a disease.

"Treating" as used herein covers any treatment of, or prevention of disease in a vertebrate, a mammal, particularly a human, and includes: preventing the disease from occurring in a subject who may be predisposed to the disease, but has not yet been diagnosed as having it; inhibiting the disease, ie., arresting its development; or relieving or ameliorating the effects of the disease, ie., cause regression of the effects of the disease.

The invention includes the use of various pharmaceutical compositions useful for ameliorating disease. The pharmaceutical compositions according to one embodiment of the invention are prepared by bringing a compound of formula I, analogue, derivatives or salts thereof and one or more pharmaceutically-active agents or combinations of compound of formula I and one or more pharmaceutically-active agents into a form suitable for administration to a subject using carriers, excipients and additives or auxiliaries.

Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 20th ed. Williams & Wilkins (2000) and The British National Formulary 43rd ed. (British Medical Association and Royal Pharmaceutical Society of Great Britain, 2002; http://bnf.rhn.net), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed., 1985).

The pharmaceutical compositions are preferably prepared and administered in dosage units. Solid dosage units include tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of the cytotoxic side effects. Various considerations are described, eg. in Langer, Science, 249: 1527, (1990). Formulations for oral use may be in the form of hard gelatin capsules, in which the active ingredient is mixed with an inert solid diluent, for example, calcium carbonate, calcium phosphate or kaolin. They may also be in the form of soft gelatin capsules, in which the active ingredient is mixed with water or an oil medium, such as peanut oil, liquid paraffin or olive oil.

Aqueous suspensions normally contain the active materials in admixture with excipients suitable for the manufacture of aqueous suspensions. Such excipients may be suspending agents such as sodium carboxymethyl cellulose, methyl cellulose, hydroxypropylmethylcellulose, sodium alginate, polyvinylpyrrolidone, gum tragacanth and gum acacia; dispersing or wetting agents, which may be (a) a naturally occurring phosphatide such as lecithin;
(b) a condensation product of an alkylene oxide with a fatty acid, for example, polyoxyethylene stearate;
(c) a condensation product of ethylene oxide with a long chain aliphatic alcohol, for example, heptadecaethylenoxycetanol;
(d) a condensation product of ethylene oxide with a partial ester derived from a fatty acid and hexitol such as polyoxyethylene sorbitol monooleate, or
(e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleaginous suspension. This suspension may be formulated according to known methods using suitable dispersing or wetting agents and suspending agents such as those mentioned above. The sterile injectable preparation may also a sterile injectable solution or suspension in a non-toxic parenterally-acceptable diluent or solvent, for example, as a solution in 1,3-butanediol. Among the acceptable vehicles and solvents which may be employed are water, Ringer's solution, and isotonic sodium chloride solution. In addition, sterile, fixed oils are conventionally employed as a solvent or suspending medium. For this purpose, any bland fixed oil may be employed, including synthetic mono-or diglycerides. In addition, fatty acids such as oleic acid may be used in the preparation of injectables.

Compounds of formula I may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Dosage levels of the compound of formula I of the present invention will usually be of the order of about 0.5 mg to about 20 mg per kilogram body weight, with a preferred dosage range between about 0.5 mg to about 10 mg per kilogram body weight per day (from about 0.5 g to about 3 g per patient per day). The amount of active ingredient which may be combined with the carrier materials to produce a single dosage will vary, depending upon the host to be treated and the particular mode of administration. For example, a formulation intended for oral administration to humans may contain about 5 mg to 1 g of an active compound with an appropriate and convenient amount of carrier material, which may vary from about 5 to 95 percent of the total composition. Dosage unit forms will generally contain between from about 5 mg to 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

In addition, some of the compounds of the invention may form solvates with water or common organic solvents. Such solvates are encompassed within the scope of the invention.

The compounds of the invention may additionally be combined with other therapeutic compounds to provide an operative combination. It is intended to include any chemically compatible combination of pharmaceutically-active agents, as long as the combination does not eliminate the activity of the compound of formula I of this invention.

The invention will now be described by way of reference only to the following general methods and experimental examples.

General Methods

Peptide synthesis

Cyclic peptide compounds of formula I are prepared according to methods described in detail in our earlier applications No. PCT/AU98/00490 and PCT/AU02/01427. An alternative method of synthesis is described in our Australian provisional application No. 2003902743. The entire disclosures of these specifications are incorporated herein by this reference. While the invention is specifically illustrated with reference to the compound AcF-[OPdChaWR] (PMX53), whose corresponding linear peptide is Ac—Phe-Orn-Pro-dCha-Trp-Arg, it will be clearly understood that the invention is not limited to this compound.

Compounds 1-6, 17, 20, 28, 30, 31, 36 and 44 disclosed in International patent application No. PCT/AU98/00490 and compounds 10-12, 14, 15, 25, 33, 35, 40, 45, 48, 52, 58, 60, 66, and 68-70 disclosed for the first time in Australian provisional application No. PCT/AU02/01427 have appreciable antagonist potency (IC50<1 µM) against the C5a receptor on human neutrophils. PMX53 and compounds 33, 45 and 60 of PCT/AU02/01427 are most preferred.

We have found that all of the compounds of formula I which have so far been tested have broadly similar pharmacological activities, although the physicochemical properties, potency, and bioavailability of the individual compounds varies somewhat, depending on the specific substituents.

The general tests described below may be used for initial screening of candidate inhibitor of G protein-coupled receptors, and especially of C5a receptors.

Drug Preparation and Formulation

The human C5a receptor antagonist AcF—[OPdChaWR] (AcPhe[Orn-Pro-D-Cyclohexylalanine-Trp-Arg]) was synthesized as described above, purified by reversed phase HPLC, and fully characterized by mass spectrometry and proton NMR spectroscopy. The C5a antagonist was prepared in olive oil (10 mg/mL) for oral dosing and in a 30% polyethylene glycol solution (0.6 mg/mL) for SC dosing. The C3a antagonist SB 290157 ($Ph_2CHCH_2OCH_2CO$-Arg-OH) has been described in detail previously (Ames at al, 2001). It was synthesized and purified by reversed phase HPLC and characterized by mass spectroscopy and NMR spectroscopy. It was prepared in a 50% propylene glycol solution (30 mg/kg) for IP injections. The glucocorticosteriod, prednisolone (Sigma, U.S.A.) was prepared in a 30% polyethylene glycol solution for SC dosing. The TNF-$\alpha$ inhibitor infliximab (Remicade®) was prepared in sterile saline (3 mg/mL) as per instructions for IV dosing. No anti-inflammatory effects were observed for propylene glycol or polyethylene glycol in rats with TNBS-induced colitis.

Receptor-Binding Assay

Assays are performed with fresh human PMNs, isolated as previously described (Sanderson et al, 1995), using a buffer of 50 mM HEPES, 1 mM $CaCl_2$, 5 mM $MgCl_2$, 0.5% bovine serum albumin, 0.1% bacitracin and 100 µM phenylmethylsulfonyl fluoride (PMSF). In assays performed at 4° C., buffer, unlabelled human recombinant C5a (Sigma) or peptide, Hunter/Bolton labelled $^{125}$I—C5a (~20 µM) (New England Nuclear, MA) and PMNs ($0.2\times10^6$) are added sequentially to a Millipore Multiscreen assay plate (HV 0.45) having a final volume of 200 µL/well. After incubation for 60 min at 4° C., the samples are filtered and the plate washed once with buffer. Filters are dried, punched and counted in an LKB gamma counter. Non-specific binding is assessed by the inclusion of 1 mM peptide or 100 nM C5a, which typically results in 10-15% total binding.

Data are analysed using non-linear regression and statistics with Dunnett post-test.

Myeloperoxidase Release Assay for Antagonist Activity

Cells are isolated as previously described (Sanderson et al, 1995) and incubated with cytochalasin B (5 µg/mL, 15 min, 37° C.). Hank's Balanced Salt solution containing 0.15% gelatin and peptide is added on to a 96 well plate (total volume 100 µL/well), followed by 25 µL cells ($4\times10^6$/mL). To assess the capacity of each peptide to antagonise C5a, cells are incubated for 5 min at 37° C. with each peptide, followed by addition of C5a (100 nM) and further incubation for 5 min. Then 50 µL of sodium phosphate (0.1M, pH 6.8) is added to each well, the plate was cooled to room temperature, and 25 µL of a fresh mixture of equal volumes of 5 dimethoxybenzidine (5.7 mg/mL) and $H_2O_2$ (0.51%) is added to each well. The reaction is stopped at 10 min by addition of 2% sodium azide. Absorbances are measured at 450 nm in a Bioscan 450 plate reader, corrected for control values (no peptide), and analysed by non-linear regression.

EXAMPLE 1

Effect of PMX53 on Inflammatory Bowel Disease

Due to the current lack of knowledge of complement involvement in IBD, we aimed to test possible inhibitory effects for PMX53 (AcF—[OPdChaWR]) in trinitrobenzene sulfonic acid (TNBS)-induced colitis in rats. For comparison, we also examined the efficacy of a C3a antagonist SB 290157 (Ames et, 2001), the corticosteroid prednisolone, and the TNF-α antibody infliximab.

PMX53 (AcF—[OPdChaWR]) was tested for its ability to ameliorate signs of damage in trinitrobenzenesulphonic acid (TNBS)-induced colitis in rats. This model has been used extensively to investigate the pathogenesis of IBD (Morris et al, 1989).

Male Wistar rats (250-300 g) were starved for 24 hours prior to being anaesthetised with ketamine (80 mg/kg i.p.) and xylazine (8 mg/kg i.p.). A 1.7 mm outer diameter polyethylene catheter was then inserted intracolonically to a distance of 8 cm from the anus. 120 mg/kg TNBS (50 mg/mL solution) along with 250 μL ethanol (100%) was then instilled to rats, which remained in the head-down position for 30 min to prevent leakage. Sham-operated rats (rats without colitis) received either saline alone or 250 μL ethanol and saline. Rats were then allowed to recover under observation.

At the completion of each experiment, rats were anaesthetized with zolazapam (50 mg/kg, IP) and xylazine (12 mg/kg, IP), and blood was collected and serum stored at −20° C. for later determination of TNF-α concentrations. Colons were dissected, and the distal 8-cm rinsed with saline and scored for clinical macroscopic damage by an independent blinded observer, using a scale of 0-13 as set out below (Bobin-Dubigeon et al, 2001). A section of the affected colon was then collected, weighed, placed in an 80° C. oven for 24 h, then reweighed and the wet-to-dry weight ratio determined as a measure of colon oedema (Rachmilewitz et al., 1989). A separate section of affected colon was also collected and homogenized with 1 mL phosphate buffered saline, sonicated for 20 seconds and centrifuged (14 000×g, 10 min). The resulting supernatant was then either stored (−20° C.) for later TNF-α determination, or used immediately in an assay for the determination of myeloperoxidase (MPO) levels. Briefly, the assay involved the addition of 20 μL substrate (o-dianisidine, 2.85 mg/mL, Sigma, U.S.A.; and 0.85% hydrogen peroxidase) to a 1:40 dilution of supernatant in phosphate buffered saline. Absorbances were then read at 450 nM, 5 min after substrate addition for 24 h samples, and 15 min after addition for 8-day samples. Results for colon MPO content were converted to absorbance units/g tissue. Additional sections of colon were removed and stored in 10% formalin for histopathological analysis. Fixed colonic samples were embedded in paraffin wax, and sections were stained using a haematoxylin and eosin stain, photographed and examined by an independent observer in a blinded fashion. Tissue and serum TNF-α levels were determined from stored samples using an enzyme-linked immunoabsorbent assay as previously described (Arumugam et al, 2002), using undiluted samples. Results for colonic TNF-α content were then converted to pg TNF-α /g tissue.

Two time-frames were chosen for this study, an acute time frame (24 hours), and a chronic time frame (8-days). During the course of the study both body weight and food eaten were measured daily. In the 24-hour study, all drug treatments commenced 2 days prior to instillation of TNBS (prevention). PMX53-, prednisolone- and combination-treated rats were treated once daily, and C3a antagonist-treated rats were dosed twice daily. Rats treated with the anti-TNF-α monoclonal antibody, infliximab, were dosed intravenously on one occasion, 2 days prior to TNBS instillation. The following treatment groups were used in the 24 hour model:

(a) PMX53 (10 mg/kg, in olive oil, oral),
(b) PMX53 (0.3 mg/kg, in 30% polyethylene glycol, subcutaneous),
(c) C3a antagonist (30 mg/kg, bid, IP),
(d) prednisolone (1 mg/kg, in 80% polyethylene glycol, subcutaneous),
(e) a combination of PMX53 (10 mg/kg, in olive oil, oral), and prednisolone (1 mg/kg, in 80% polyethylene glycol, subcutaneous), and
(f) infliximab (1 mg/kg, in saline, intravenous).

In the 8-day study, drug-treated rats were treated both prior to colitis induction (2 days before; prevention) or following colitis induction (24 hours after; reversal). The following treatment groups were used in the 8-day study:

(a) PMX53 (10 mg/kg, in olive oil, oral, both pre- and post-induction),
(b) PMX53 (0.3 mg/kg, in 30% polyethylene glycol, subcutaneous, pre-induction only),
(c) PMX53 (1 mg/kg, in olive oil, oral, post-induction only),
(d) prednisolone (1 mg/kg, in 80% polyethylene glycol, subcutaneous, both pre- and post-induction),
(e) a combination of PMX53 (10 mg/kg, in olive oil, oral) and prednisolone (1 mg/kg, in 80% polyethylene glycol, subcutaneous) (pre-induction only), and
(f) infliximab (1 mg/kg, in saline, intravenous, pre-induction only).

Colons were then macroscopically scored under blind conditions on a scale of 1-14, as follows:

| Ulceration | Diarrhea | Adhesions |
| --- | --- | --- |
| 0—No damage | 0—Absent | 0—Absent |
| 1—Focal hyperemia | 1—Mild | 1—Mild |
| 2—Hyperemia and bowel thickening | 2—Severe | 2—Severe |
| 3—Ulceration at 1 site | | |
| 4—Ulceration at 2 sites | | |
| 5—Ulceration >1 cm | | |
| 6-10—Ulceration >2 cm; | | |
| increase score by 1 for each additional cm. | | |

The results for a number of parameters are summarized in FIGS. 1 to 7. All experimental results are expressed as means±standard error of the mean (SEM). Data analysis was performed using GraphPad Prism 3.0 software (GraphPad Software, Inc. USA). Statistical comparisons were made between drug-treated groups and colitis control animals using a one-way analysis of variance followed by a Dunnett comparison post-test analysis. Statistical significance was assessed at $P<0.05$.

Mortality rate: As shown in FIG. 1, induction of colitis in drug-free rats resulted in a high mortality rate, 39%, beginning 2 days after TNBS administration. All drug treatments, except for prednisolone post-treatment, resulted in a decrease in mortality (n=8-16) compared with drug-free colitis control rats (n=13). No deaths were recorded in sham-operated animals (n=4). Rats treated with the C5a antagonist either prior to induction (10 mg/kg/day oral and 0.3 mg/kg/day SC) or 24 h after induction (1 or 10 mg/kg/day oral) had improved survival, with mortality rates of 20% or less. Rats pre-treated with the corticosteroid prednisolone (1 mg/kg/day SC) had a similar reduction in mortality rate, to 11%; however, post-treatment with prednisolone had no significant effect on reducing mortality. Infliximab pre-treatment (3 mg/kg IV) reduced the mortality to 20%, which was less effective than the C5a antagonist (at 10 mg/kg oral or 0.3 mg/kg SC) or prednisolone pre-treatment. There were no deaths among rats pre-treated with a combination of the C5a antagonist (10 mg/kg/day oral) and prednisolone (1 mg/kg/day SC), or in rats pre-treated with the C5a antagonist at 0.3 mg/kg SC.

Food Intake: No significant improvements in food consumption were seen after 24 h following drug treatment compared with drug-free colitis control rats. After 8 days all drug-treated rats except for prednisolone post-treated rats ate significantly more food than drug-free colitis control rats. As shown in FIG. 2A, colitis induction resulted in a decrease in the consumption of food in all TNBS-administered rats compared to sham-operated rats after 24 h. Drug treatment did not significantly improve food intake over 24 h.

Over 8 days, as illustrated in FIG. 2B, drug-free rats were still eating less food than sham-operated rats. Rats treated with the C5a antagonist either prior to induction (10 mg/kg/day oral and 0.3 mg/kg/day SC) or 24 h after induction (1 or 10 mg/kg/day oral) ate significantly more food than colitis control rats, and were consuming similar levels of feed to sham-operated rats at Day 8 ($P<0.05$;). Rats pre-treated with prednisolone (1 mg/kg/day SC) also ate significantly more food than colitis control rats after 8 days ($P<0.05$); however, rats post-treated with this drug had no improvement in food consumption ($P>0.05$). Rats pre-treated with infliximab (3 mg/kg IV) also ate significantly more food than drug-free rats after 8 days, as did rats pre-treated with a combination of the C5a antagonist (10 mg/kg/day oral) and prednisolone (1 mg/kg/day SC) ($P<0.05$).

Body weight: No significant reduction in weight loss was seen after 24 h following drug treatment compared with drug-free colitis control rats. After 8 days only rats treated with the C5a antagonist gained significant weight compared with drug-free colitis control rats. All rats receiving TNBS had considerable weight loss at 24 h post-induction compared to sham-operated rats, as shown in FIG. 3A. Drug treatment did not significantly affect this weight loss over 24 h.

Over the 8-day study period, as shown in FIG. 3B, drug-free rats continued to lose weight with the mean weight loss at Day 8 being −21±8 g (n=8). Rats treated with the C5a antagonist either prior to colitis induction (10 mg/kg/day oral and 0.3 mg/kg/day SC) or 24 h after induction (1 or 10 mg/kg/day oral) gained substantial weight over the 8 days, with significantly higher weights compared to colitis control rats ($P<0.05$). In contrast, rats either pre-treated or post-treated with prednisolone (1 mg/kg/day SC), or rats pre-treated with a combination of the C5a antagonist (10 mg/kg/day oral) and prednisolone (1 mg/kg/day SC), lost weight over the 8 days, with no significant difference compared to colitis control rats on Day 8 ($P>0.05$). Rats pre-treated with infliximab (3 mg/kg IV) had only a small weight gain at Day 8; however, these levels were not significantly higher than colitis control rats ($P>0.05$).

Macroscopic Score: Colons were examined macroscopically for signs of haemorrhage and ulceration by an independent observer, in a blinded fashion, using a previously established scoring system (Bobin-Dubigeon et al, 2001). After 24 h, all drug treatments except for infliximab resulted in a significant improvement in macroscopic scores compared with drug-free colitis control rats. After 8 days, all drug treatments except for prednisolone post-treatment resulted in a significant improvement in macroscopic scores compared with drug-free colitis control rats. Sham-operated animals displayed no appreciable macroscopic damage.

As shown in FIG. 4A, after 24 h colons from all TNBS-treated rats were found to have extensive haemorrhage, oedema and early ulcer formation. No adhesions were observed, and diarrhoea was minimal. Drug-free rats had a mean macroscopic score of 7.2±0.5 (n=12) at 24 h. Pre-treatment of rats by any drug in the 24 h study resulted in reductions in macroscopic scores, with a significant improvement seen in all treatment groups except for infliximab ($P<0.05$). As shown in FIG. 4B, after 8 days colons from TNBS— treated rats had considerably greater damage than at 24 h, indicating that pathology was progressive. Although the colons had less haemorrhage, ulcer formation was extensive and adhesions and diarrhoea were common. Colitis control rats had a mean macroscopic score of 11.5±0.8 (n=12) at Day 8. Rats treated with the C5a antagonist either prior to induction (10 mg/kg/day oral and 0.3 mg/kg/day SC) or 24 h after induction (1 or 10 mg/kg/day oral), had significantly improved macroscopic scores compared to colitis control rats, as did prednisolone pre-treated rats (1 mg/kg/day, SC) ($P<0.05$). Rats pre-treated with infliximab (3 mg/kg IV) also had significantly decreased scores on Day 8 ($P<0.05$). Rats post-treated with prednisolone (1 mg/kg/day, SC) did not have any improvement in macroscopic scores on Day 8 ($P>0.05$).

Colon MPO: After 24 h, only rats treated with either the C5a antagonist or a combination of the C5a antagonist and prednisolone, had a significant improvement in colon MPO levels compared with drug-free colitis control rats. After 8 days, all drug treatments except for prednisolone post-treatment resulted in a significant improvement in colon MPO levels compared with drug-free colitis control rats. As shown in FIG. 5A, levels of MPO in the colons of drug-free rats were substantially higher at 24 h than in sham-operated rats. Levels of this enzyme were reduced in all drug-treated rats after 24 h, with a significant improvement in rats either pre-treated with the C5a antagonist (10 mg/kg/day oral or 0.3 mg/kg/day SC) or with a combination of the C5a antagonist (10 mg/kg/day oral) and prednisolone (1 mg/kg/day SC) ($P<0.05$).

As shown in FIG. 5B, after 8 days the levels of colonic MPO in TNBS-administered rats were further reduced compared with 24 h. In rats treated with the C5a antagonist either prior to induction (10 mg/kg/day oral and 0.3 mg/kg/day SC) or 24 h after induction (1 and 10 mg/kg/day oral), or in rats pre-treated with a combination of the C5a antagonist (10 mg/kg/day oral) and prednisolone (1 mg/kg/day SC), the levels of colonic MPO were reduced to similar levels to those of the sham-operated animals after 8 days ($P<0.05$). Rats pre-treated with either prednisolone (1 mg/kg/day SC) or infliximab (3 mg/kg IV) also had significantly reduced colonic MPO levels after 8 days, although the extent of improvement was not as great as in rats treated with the C5a antagonist ($P<0.05$). Rats post-treated with prednisolone (1 mg/kg/day SC) did not show any improvement in colonic MPO levels ($P>0.05$).

Figure 6:
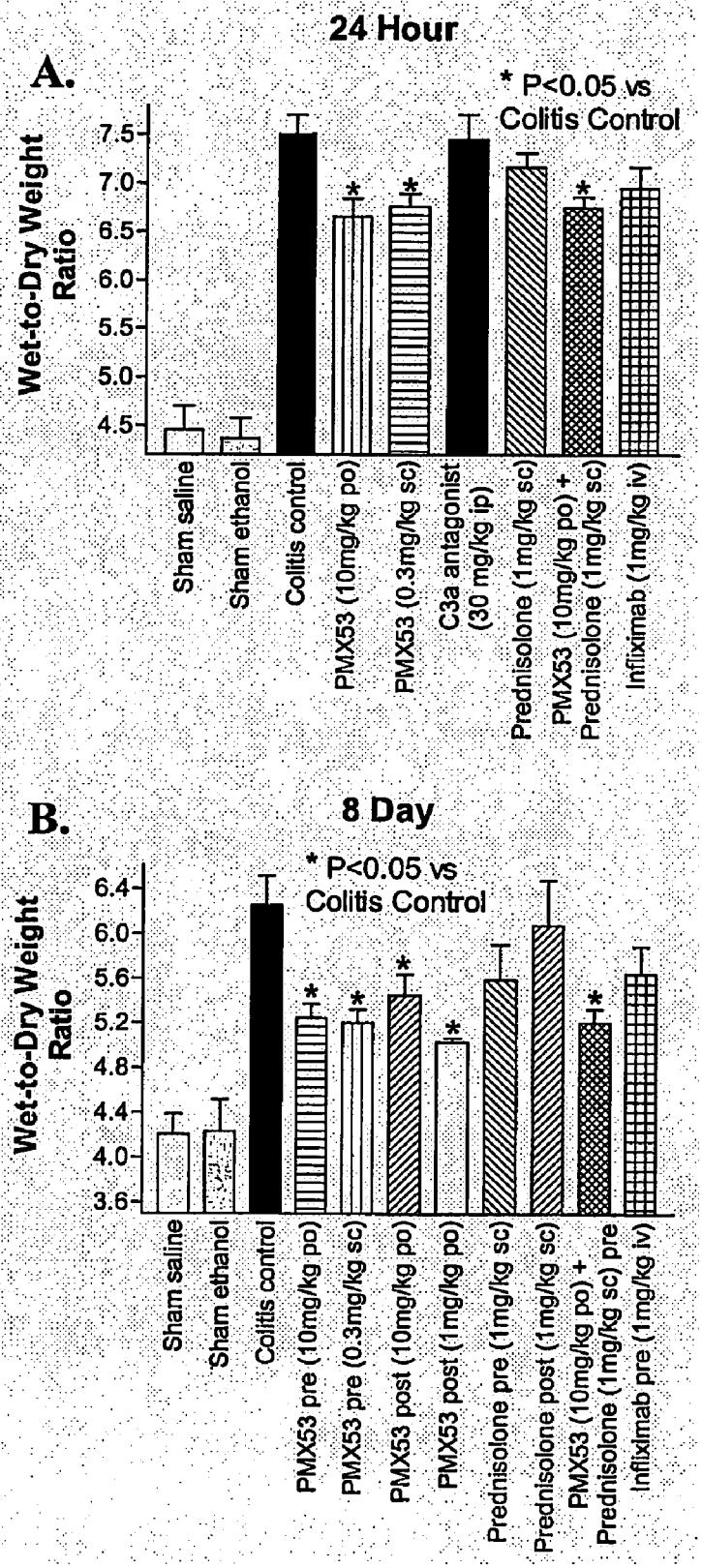
FIG. 6 shows the effect on colon oedema levels in 24 h and 8 day studies. [A] 24 h; [B] 8 days. Data represent the mean±SEM (n=4-12). *$P<0.05$ drug-treated rats vs. colitis control. pre=pre-treatment; post=post-treatment.

Colonic oedema: Colon oedema, determined by wet-to-dry weight ratios, was measured at either 24 h or 8 days. The results are shown in FIG. 6. After both 24 h and 8 days, only rats treated with either the C5a antagonist, or a combination of the C5a antagonist and prednisolone, had a significant improvement in colon wet-to-dry weight ratios, compared with drug-free colitis control rats. As shown in FIG. 6A, wet-to-dry weight ratios of colons from TNBS-administered rats were considerably increased compared to sham-operated rats after 24 h, indicating oedema. At this time point, only rats which had been pre-treated with the C5a antagonist (10 mg/kg/day oral or 0.3 mg/kg/day SC) or with a combination of the C5a antagonist (10 mg/kg/day oral) and prednisolone (1 mg/kg/day SC), had a significant reduction in wet-to-dry weight ratios compared to colitis control rats (P<0.05). The C3a antagonist did not have a significant effect.

As shown in FIG. 6B, after 8 days the level of colonic oedema in TNBS-administered rats was still considerably higher than for sham-operated rats, although lower than that seen at 24 h. There were significant reductions in wet-to-dry weight ratios in rats treated with the C5a antagonist, either prior to induction (10 mg/kg/day oral and 0.3 mg/kg/day SC) or 24 h after induction (1 and 10 mg/kg/day oral), as well as in rats pre-treated with a combination of the C5a antagonist (10 mg/kg/day oral) and prednisolone (1 mg/kg/day SC) in this 8 day time frame (P<0.05). Post-treatment with prednisolone (1 mg/kg/day SC) had no effect on reducing oedema, whilst prednisolone (1 mg/kg/day SC) and infliximab (3 mg/kg IV) pre-treated rats had no significant reductions compared to colitis control rats (P>0.05).

Figure 7:
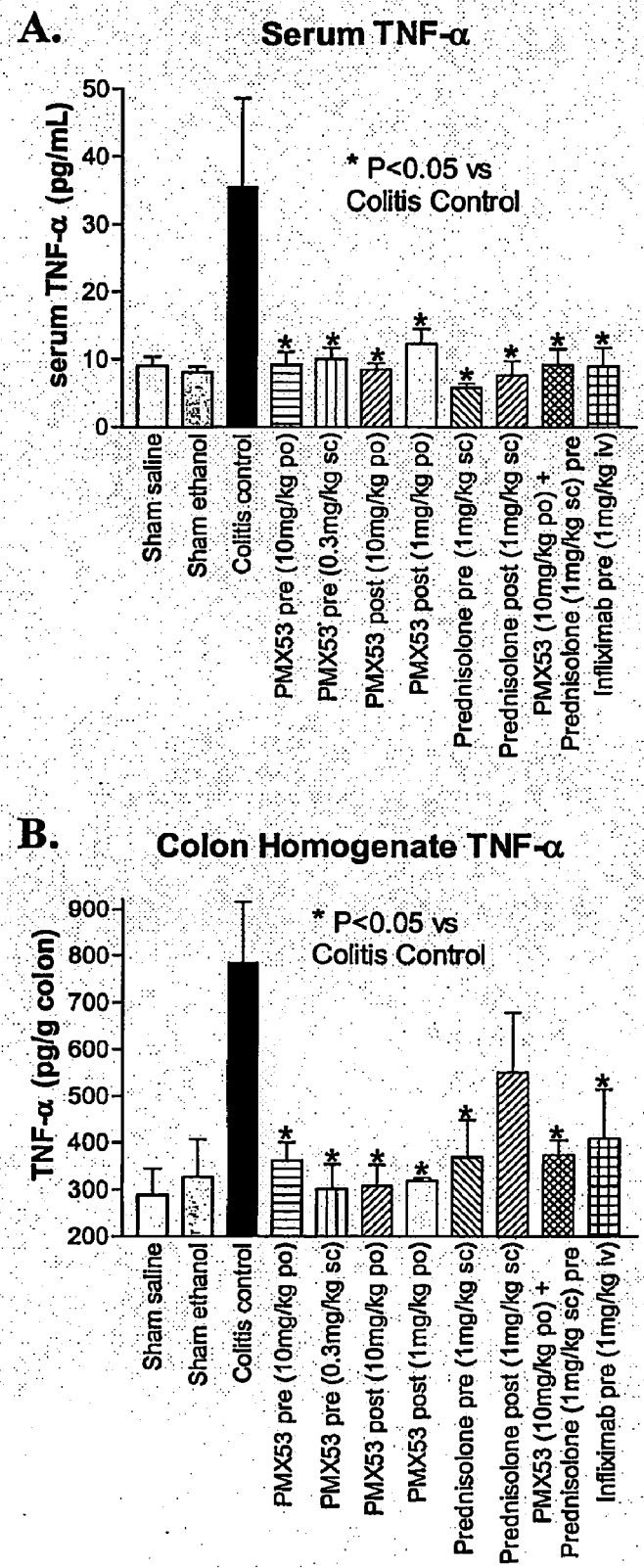
FIG. 7 shows the effect on serum and colonic TNF-α levels after 8 days. Data represent the mean±SEM (n=4-12).
[A] Serum; [B] Colonic Tissue.
*$P<0.05$ drug-treated rats vs. colitis control. pre=pre-treatment; post=post-treatment.

Serum and Tissue TNF-α Levels: TNF-α levels were then measured after 8 days in either serum or colonic tissue. The results are illustrated in FIG. 7. Serum levels of TNF-α were increased 35 in drug-free colitis control animals, and all drug treatments significantly reduced these levels. All drug treatments, except for prednisolone post-treatment, significantly improved colonic TNF-α levels compared with drug-free colitis control rats. Levels of serum TNF-α and colonic tissue TNF-α were not increased in TNBS-treated rats compared to sham-operated rats after 24 h. As shown in FIG. 7A, after 8 days serum TNF-α levels in colitis control rats were increased compared to sham-operated rats. All drug-treated rats had similar serum TNF-α levels to sham-operated rats, and these levels were significantly reduced compared to colitis control levels (P<0.05). Colon tissue homogenate TNF-α levels; shown in FIG. 7B, were also increased in drug-free rats compared to sham-operated animals. All drug-treated rats had significantly lower tissue levels of this cytokine, compared to colitis control rats (P<0.05), except for prednisolone post-treated rats (1 mg/kg/day SC), which had no significant reduction (P>0.05).

Histopathology: Stained sections of colon were examined for signs of pathology by an independent observer in a blinded fashion. At 24 h after TNBS administration, sections of colons showed signs of acute inflammation. In mild cases there was oedema of the submucosal layers of the bowel and infiltration, predominantly by neutrophils, into the mucosa and submucosa. In more severe cases there was necrosis of the colonic mucosal cells, and more severe oedema and inflammatory cell infiltration. No observable improvements were seen in sections of colons from drug-treated rats compared to drug-free colitis control rats in this acute time frame.

At 8 days after TNBS challenge there was evidence of healing, with affected mucosa being replaced by fibrous tissue. There was PMN infiltration of affected tissues. Where discrete ulcers were identified, the bordering mucosa appeared normal, although there was generalised submucosal inflammation, consisting of inflammatory cells and mild oedema. Colon sections from drug-free colitis control rats showed the most severe pathology after 8-days (FIG. 8B). In comparison, sections of colon from sham-operated rats showed minimal signs of damage (FIG. 8A). After 8 days sections of colons from all rats which had been pre-treated with either the C5a antagonist, prednisolone, infliximab or a C5a antagonist/prednisolone combination showed an improvement in pathology compared to drug-free rats. Sections of colons from rats which had been post-treated with the C5a antagonist (10 mg/kg/day PO) also showed an improvement in disease pathology after 8 days, indicated by less ulcer formation, oedema, inflammatory cell infiltration, no perforations and intact mucosal layers compared with sections from drug-free rats (FIG. 8C). In contrast, sections of colons from rats which had been post-treated with prednisolone (1 mg/kg/day SC) showed no improvement in disease pathology compared with drug-free rats (FIG. 8D).

In the 24-hour study, PMX53-treated rats had significantly lower colon macroscopic scores and higher body weights and food intake.

The level of colon oedema, neutrophil accumulation and colon TNF-α levels were also significantly reduced. In comparison to prednisolone and infliximab, which are currently used in therapy for IBD, PMX53-treated rats displayed a greater inhibition of the parameters measured. These results show that blockade of the inflammatory protein C5a by PMX53 significantly improves disease pathology in the acute 24-hour model of IBD, to an extent at least as great as that achieved by prednisolone or infliximab.

In the 8-day study, PMX53 pre-treated rats as well as post-treated rats lost significantly less body weight and ate significantly more food compared to colitis control animals. These rats also had significantly lower colon macroscopic scores, colon oedema, neutrophil accumulation and colon TNF-α levels. Most importantly, PMX53-treated rats also had reduced mortality compared to colitis control rats. In comparison, only prednisolone pre-treated rats displayed any improvement in the disease parameters measured. Infliximab-treated rats also had significantly reduced disease parameters, however to a lesser extent than those observed in PMX53-treated rats.

Figure 8:
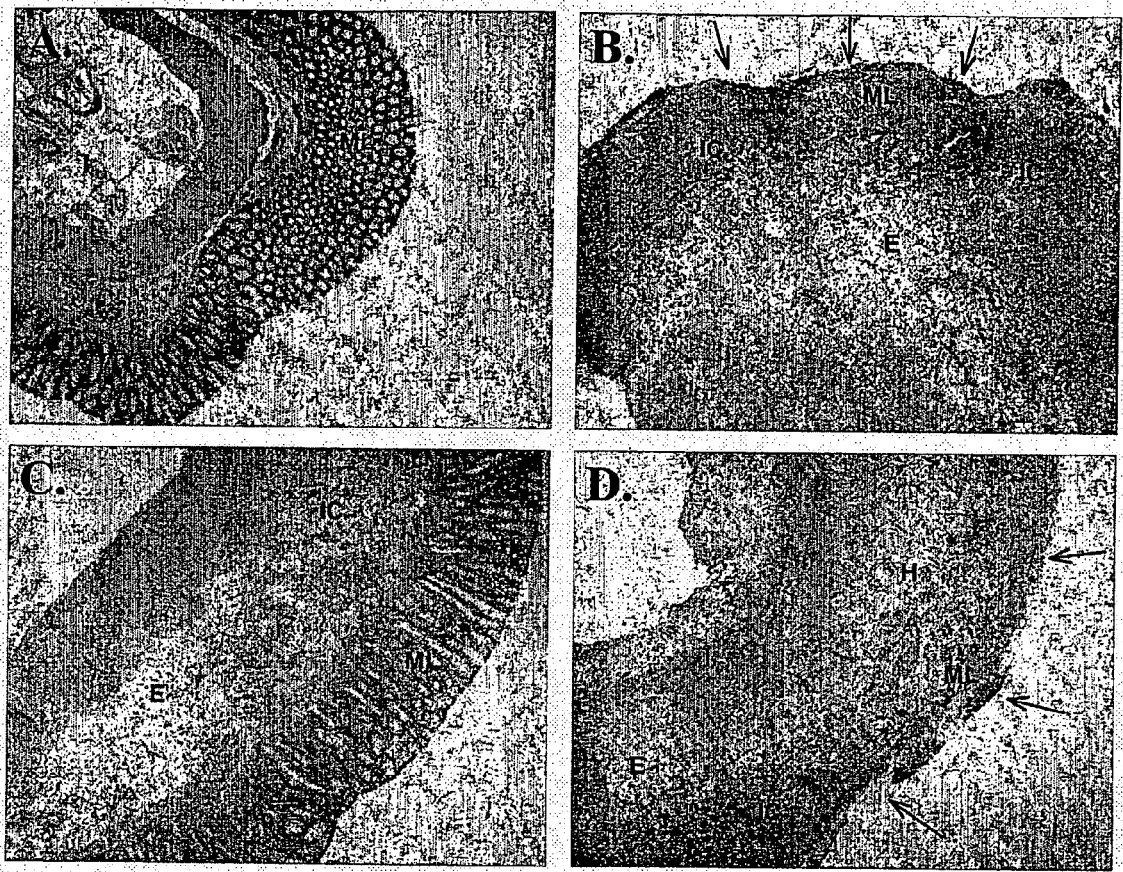
FIG. 8 shows sections of colons from rats in the 8 day study, stained with haematoxylin and eosin (×40 magnification). Images are typical, and representative of each study group.
[A] saline injected, sham-operated rat with intact epithelial and mucosal layer (ML);
[B] TNBS drug-free colitis control rat with extensive damage including inflammatory cell (IC) infiltration, oedema (E), and the complete destruction of ML architecture (indicated by arrows);
[C] TNBS C5a antagonist (10 mg/kg/day, oral) post-treated rat with IC infiltration and E, but with intact ML; and [D] TNBS prednisolone (1 mg/kg/day, SC) post-treated rat with IC infiltration, E, extensive haemorrhage (H) and erosion of ML (indicated by arrows).

Histologically, colonic sections of rats treated with PMX53 displayed a decrease in inflammatory cell accumulation and haemorrhage formation, and this is shown in FIG. 8. These results surprisingly show that blockade of the inflammatory protein C5a by PMX53 both prevents and reverses disease pathology in a rat model of chronic colitis. This effect of reversal of pathology was not seen in rats treated with prednisolone.

In summary, these studies demonstrate for the first time that an inhibitor of the complement system has beneficial effects in an established model of IBD. The improvements seen with PMX53 were greater than those seen with prednisolone or infliximab. This indicates that PMX53 will be useful in the clinical treatment of IBD.

EXAMPLE 2

Further Studies in Animal Models

An 8-day time frame is used in further animal studies, as this provides the most significant and clinically relevant pathology. All drugs are administered 24 hours after colitis induction (reversal therapy), and then daily throughout the study period. PMX53 is administered at doses of 0.1, 0.3, 1 and 10 mg/kg in mineral oil via per rectum (p.r.) dosing. PMX53 is also administered orally at 0.1, 0.3, 1 and 10 mg/kg, in an enteric-coated capsule.

Analogues of PMX53 are also tested at various doses ranging from 0.1-10 mg/kg, in olive oil solvent, to assess their effectiveness compared with PMX53. In the first instance the following analogues are tested:

PMX205: Hydrocinnamate-[OPdChaWR]

PMX73: AcF—[OPdPheWR]

PMX201: AcF—[OPdChaWCitrulline]

These compounds are administered at 0.3, 1, 3 and 10 mg/kg/day post-treatment in the 8 day study.

In addition to the TNBS model system, felines and particularly canines suffer from a variety of inflammatory enteropathies which have some similarities to IBD in humans (Tams, 1993; German et al, 2003). These include enterocolitis, canine plasmacytic-lymphocytic colitis, protothecal colitis, and histocytic ulcerative colitis. PMX53 and its analogues are also tested in these conditions.

EXAMPLE 3

Assessment of Clinical Efficacy

The clinical efficacy in humans of compounds found to be effective in animal models is determined using standard clinical trial methods.

For example, a randomized, placebo-controlled, phase II trial in the treatment of patients with mild-to-moderate Crohn disease typically employs at least two dose levels of the test compound. A decrease of greater than 70 points on the Crohn's Disease Activity Index (CDAI), a standardized tool designed to measure disease activity specifically, is a primary endpoint for indication of efficacy. Disease remission is a secondary endpoint. A treatment effect advantage is established if significantly more recipients of the test compound than placebo recipients are found to have CDAI scores consistent with symptom resolution during an acute exacerbation of the inflammatory bowel disease.

For ulcerative colitis, the effects of treatment with the test compound are assessed in patients with symptoms of active ulcerative colitis who have either not previously been treated, or who are also receiving standard medical treatment. The endpoints are induction of complete remission or significant improvement in signs and symptoms of ulcerative colitis, as reflected in changes in a colitis activity index (CAI) score. The CAI score assesses stool frequency, rectal bleeding, endoscopic appearance of the colon, and includes a physician's global assessment.

For each condition the adverse effect and tolerability profiles of the test compound are also monitored.

DISCUSSION

Cyclic peptides have several important advantages over acyclic peptides as drug candidates (Fairlie et al 1995, Fairlie et al, 1998, Tyndall and Fairlie, 2001).

The cyclic compounds described in this specification are stable to proteolytic degradation for at least several hours at 37° C. in human blood or plasma, in human or rat gastric juices, or in the presence of digestive enzymes such as pepsin, trypsin and chymotrypsin. In contrast, short linear peptides composed of L-amino acids are rapidly degraded to their component amino acids within a few minutes under these conditions. A second advantage lies in the constrained single conformations adopted by the cyclic and non-peptidic molecules, in contrast to acyclic or linear peptides, which are flexible enough to adopt multiple structures in solution other than the one required for receptor-binding. Thirdly, cyclic compounds such as those described in this invention are usually more lipid-soluble and more pharmacologically bioavailable as drugs than acyclic peptides, which can rarely be administered orally. Fourthly, the plasma half-lives of cyclic molecules are usually longer than those of peptides.

Models of IBD typically involve the intra-colonic administration of an inflammatory or haptenising agent. The TNBS-induced colitis model used herein is a simple, reliable model which has been widely used to examine the efficacy of various candidate drugs for treatment of IBD.

We found that 24 h after TNBS administration, rat colons displayed large areas of haemorrhage, oedema and inflammatory cell infiltration. However, in this acute model we found it difficult to detect any significant therapeutic effects for drugs compared to drug-free, colitis-bearing rats. In contrast, 8 days after colitis induction the colons of rats showed considerably greater damage than seen at 24 h, and it became easier to compare the effects of different drugs. The increased damage observed at 8 days confirms that the pathology continues to develop, even after the initiating agent has been metabolized. In this chronic model a substantial proportion of the rats died, and elevated levels of TNF-α in serum and colonic tissue were observed in the surviving rats. The 8 day experiment also allowed the inclusion of post-induction drug treatments, to determine whether drugs could be used to treat and perhaps reverse the developing disease.

We used both the 24 h and 8 day time frames to compare the efficacy of two newly-developed antagonists of the C3a and C5a receptor with that of the steroid prednisolone and the TNF-α inhibitor infliximab. All the drugs tested were effective at reducing some, or all, of the parameters measured. However, the C5a antagonist was found to be superior to the other drugs.

Corticosteroids, such as prednisolone, are commonly prescribed therapies in the treatment of IBD. They are powerful drugs which act at the genetic level, resulting in the down-regulation of various pro-inflammatory mediators, such as cytokines, as well as immune pathways. Because of their non-specific actions corticosteroids have numerous serious side effects, and must be used with caution in patients, particularly for chronic treatment. In our study, prednisolone pre-treatment was effective at reducing the majority of parameters measured, as expected. However, prednisolone-treated rats lost considerable body weight. This was attributed to catabolism, a major side effect with steroid therapy. Although steroids are widely used in colitis therapy, it is of interest that rats treated with steroid 24 h after the induction of colitis showed no appreciable therapeutic effects. Because of the time it takes for steroids to become effective, this may have been too late for any appreciable effect of prednisolone on disease pathology. Alternatively, the lack of effect may have resulted from the tendency of steroid treatments to inhibit natural healing processes associated with disease pathology.

The proinflammatory cytokine TNF-α is thought to be a major contributor to the pathology of IBD. Recent advances in drug development have produced various antibodies which block the effects of this cytokine (Muller, 2002). One of these antibodies, infliximab, has been reported to be effective in reducing IBD pathology, and is now currently available for the treatment of IBD in various countries. Such antibody-based therapies have delivery problems in the clinic, and are significantly more expensive than other drug therapies (Valle et el, 2001). The efficacy of infliximab in an animal model of IBD has not to our knowledge been previously described. We therefore used this compound as a comparator drug for the C5a and C3a receptor antagonists. Although pre-treatment of rats with infliximab did reduce the severity of lesions, it was not as effective as the C5a antagonist or prednisolone. Infliximab was more effective in rats treated for 8 days than for rats in the 24 h study. Given that detectable increases in serum and colonic tissue TNF-α levels were only seen in the 8-day study, the effect of TNF-α inhibition by this compound would be expected to be minimal during the acute stages of the disease.

Abnormal complement activity is suspected to be important in the pathology of IBD, although there is limited evidence for this to date. In this study, we examined the efficacy of the C3a antagonist SB 290157. This compound has been recently reported to be an antagonist of the human C3a receptor, and to show activity in various in vitro and in vivo assays (Mollnes et al, 2002; Ames et al, 2001). We found that this antagonist was effective in reducing some of the parameters measured in the 24 h study. Most importantly, it reduced the intensity of macroscopic damage compared to colitis control rats. The dosage regime chosen in our study (30 mg/kg i.p. twice daily) was the same as used in previous in vivo studies, and this high dose appears to be necessary to obtain therapeutic effects with this compound (Ames et al, 2001). Because of the need to inject animals intraperitoneally twice daily, the drug was not evaluated in the 8-day model. Despite the inhibitory effects seen with SB 290157 after 24 h, further studies will need to be performed over a longer time to identify the precise role of C3a in TNBS-induced colitis.

The cyclic peptide C5a antagonist PMX53 (AcF—[OPd-ChaWR]) was the most effective agent used in this study. We found that pre-treatment of rats with the C5a antagonist either orally or SC markedly reduced all the disease markers measured. Rats which were treated orally 24 h after colitis was established also had a significant reduction in all disease markers. This C5a antagonist has been shown to be specific for the C5a receptor in human, rat and dog (Woodruff et al, 2001), and to be specific for the C5a receptor over other related human receptors (Finch et al, 1999). In particular, PMX53 does not bind to the C3a receptor (Finch et al, 1999), and has no effect on the formation of the membrane attack complex (Arumugam et al, 2003). The increased efficacy seen with the C5a antagonist over the C3a antagonist, at least in the 24 h study, is consistent with the higher potency and the greater pro-inflammatory activity of C5a compared to C3a in vivo.

The greater efficacy of the C5a antagonist compared to infliximab may be explained by the central role of C5a in the inflammatory cascade. It is known that C5a induces the release of not only TNF-α, but also a host of other inflammatory cytokines and various mediators which are reportedly also involved in IBD (Haynes et al, 2002; Mollnes et al, 2002). This C5a antagonist is also known to prevent formation of a number of these mediators (Finch et al, 1999; Haynes et al, 2002), which probably explains its superior efficacy to infliximab, which solely inhibits TNF-α. We have now shown that an antagonist of human C5a receptors is also a potent and effective treatment for IBD in a rat model.

When rats were pretreated with a combination of the C5a antagonist and prednisolone, no greater reduction in disease markers was observed than with the C5a antagonist alone. This suggests a common downstream regulation of inflammatory mediators.

In summary, this study demonstrates a significant role for the complement components C3a and C5a, and especially C5a, in the pathogenesis of TNBS-induced colitis in rats. Complement may therefore have a pivotal role in the development of human IBD. This should encourage the development of anti-complement-based therapies. The potent therapeutic effects of the orally active human C5a antagonist AcF—[OPdChaWR], and its greater efficacy compared to prednisolone and infliximab, support a role for the use of C5a antagonists in the treatment of IBD in humans.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Ames R S, Lee D, Foley J J, Jurewicz A J, Tornetta M A, Bautsch W, Settmacher B, Klos A, Erhard K F, Cousins R D, Sulpizio A C, Hieble J P, McCafferty G, Ward K W, Adams J L, Bondinell W E, Underwood D C, Osborn R R, Badger A M, Sarau H M. J. Immunol. 2001, 166(10):6341-8.

Fairlie, D. P., Wong, A. K.; West, M. W. Curr. Med. Chem., 1998, 5, 29-62.

Fairlie, D. P., Abbenante, G. and March, D. Curr. Med. Chem., 1995 2 672-705.

Gerard, C and Gerard, N. P. Ann. Rev. Immunol., 1994 12 775-808.

German, A. J., Hall, E. J., and Day, M. J. J Vet Intern Med. 2003 January-February;17(1):8-20.

Konteatis, Z. D., Siciliano, S. J., Van Riper, G., Molineaux, C. J., Pandya, S., Fischer, P., Rosen, H., Mumford, R. A., and Springer, M. S. J. Immunol., 1994 153 4200-4204.

Mollnes T E, Brekke O L, Fung M, Fure H, Christiansen D, Bergseth G, Videm V, Lappegard K T, Kohl J, Lambris J D. Blood. 2002 Sep. 1;100(5):1869-77.

Morris G P, Beck P L, Herridge M S, Depew W T, Szewczuk M R, Wallace J L. Gastroenterol. 1989;96:795-803.

Nielsen O H, Rask-Madsen J. Scand J Gastroenterol Suppl. 1996;31:149-159.

Sanderson, S. D., Kirnarsky, L., Sherman, S. A., Vogen, S. M., Prakesh, O., Ember, J. A., Finch, A. M. and Taylor, S. M. J. Med. Chem., 1995 38 3669-3675.

Tams, T. R. Vet Clin North Am Small Anim Pract., 1993 23:569-86.

Tyndall, J. D. A.; Fairlie, D. P. Curr. Med. Chem. 2001, 8, 893-907.

The invention claimed is:

1. A method of treating ulcerative colitis, comprising administering an effective amount of the compound AcPhe[Orn-Pro-D-Cyclohexylalanine-Trp-Arg] to a subject in need thereof.

2. A method of relieving or ameliorating the effects of ulcerative colitis, comprising administering an effective amount of the compound AcPhe[Orn-Pro-D-Cyclohexylalanine-Trp-Arg] to a subject in need thereof.

3. The method of claim 1 or claim 2, wherein said compound has potent antagonist activity at sub-micromolar concentrations.

4. The method of claim 1 or claim 2, wherein said compound has a receptor affinity $IC_{50}$ <25 μM, and an antagonist potency $IC_{50}$ <1 μM.

5. The method of claim 1 or claim 2, wherein said subject is human.

6. The method of claim 1 or claim 2, wherein said compound is administered to said subject in conjunction with one or more other agents for the treatment of ulcerative colitis.

7. The method of claim 6, wherein said one or more other agents comprise an inhibitor of TNF-α or C3a.

8. The method of claim 7, wherein said inhibitor of TNF-α is infliximab.

9. The method of claim 7, wherein said inhibitor of C3a is compound SB 290157, which has the formula $(Ph_2CHCH_2OCH_2CO\text{-Arg-OH})$.

* * * * *